United States Patent
Chu et al.

(10) Patent No.: US 7,878,969 B2
(45) Date of Patent: Feb. 1, 2011

(54) PELVIC FLOOR REPAIR SYSTEM

(75) Inventors: Michael S. H. Chu, Brookline, MA (US); Brett Nowlin, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 540 days.

(21) Appl. No.: 11/493,148

(22) Filed: Jul. 25, 2006

(65) Prior Publication Data

US 2007/0055095 A1 Mar. 8, 2007

Related U.S. Application Data

(60) Provisional application No. 60/702,539, filed on Jul. 25, 2005, provisional application No. 60/702,540, filed on Jul. 25, 2005, provisional application No. 60/715,362, filed on Sep. 8, 2005.

(51) Int. Cl.
*A61F 2/02* (2006.01)

(52) U.S. Cl. .............................................. 600/30

(58) Field of Classification Search ............. 600/29–31, 600/37; 128/885, 897; 606/228, 151, 232, 606/139; 623/23.72
See application file for complete search history.

(56) References Cited

U.S. PATENT DOCUMENTS

| | | | |
|---|---|---|---|
| 5,840,011 A | 11/1998 | Landgrebe et al. | |
| 5,899,909 A | 5/1999 | Claren et al. | |
| 6,530,943 B1 | 3/2003 | Hoepffner et al. | |
| 6,638,210 B2 | 10/2003 | Berger | |
| 6,652,450 B2 | 11/2003 | Neisz et al. | |
| 6,808,487 B2 | 10/2004 | Migliari | |
| 6,986,780 B2 | 1/2006 | Rudnick et al. | |
| 7,083,637 B1* | 8/2006 | Tannhauser | 606/228 |
| 7,527,588 B2* | 5/2009 | Zaddem et al. | 600/29 |
| 2001/0049467 A1 | 12/2001 | Lehe et al. | |
| 2003/0078604 A1* | 4/2003 | Walshe | 606/151 |
| 2003/0176762 A1 | 9/2003 | Kammerer | |
| 2004/0039453 A1 | 2/2004 | Anderson et al. | |
| 2004/0068159 A1 | 4/2004 | Neisz et al. | |
| 2004/0087970 A1* | 5/2004 | Chu et al. | 606/119 |
| 2004/0249397 A1 | 12/2004 | Delorme et al. | |
| 2004/0249473 A1 | 12/2004 | Delorme et al. | |
| 2005/0245787 A1 | 11/2005 | Cox et al. | |
| 2005/0250977 A1 | 11/2005 | Montpetit et al. | |
| 2005/0261547 A1* | 11/2005 | Bouffier | 600/37 |
| 2005/0278037 A1 | 12/2005 | Delorme et al. | |
| 2006/0058575 A1 | 3/2006 | Zaddem et al. | |

FOREIGN PATENT DOCUMENTS

| | | |
|---|---|---|
| FR | 2 852 818 | 10/2004 |
| WO | WO-02/32284 A2 | 4/2002 |
| WO | WO-2004/016196 | 2/2004 |

* cited by examiner

*Primary Examiner*—Charles A Marmor, II
*Assistant Examiner*—Christine D Hopkins

(57) ABSTRACT

Systems, method, and devices related to surgically implantable supportive slings are presented herein. More specifically, in various embodiments, the systems, devices and methods relate to a surgically implantable supportive sling adapted to anchor in patient tissue.

9 Claims, 19 Drawing Sheets

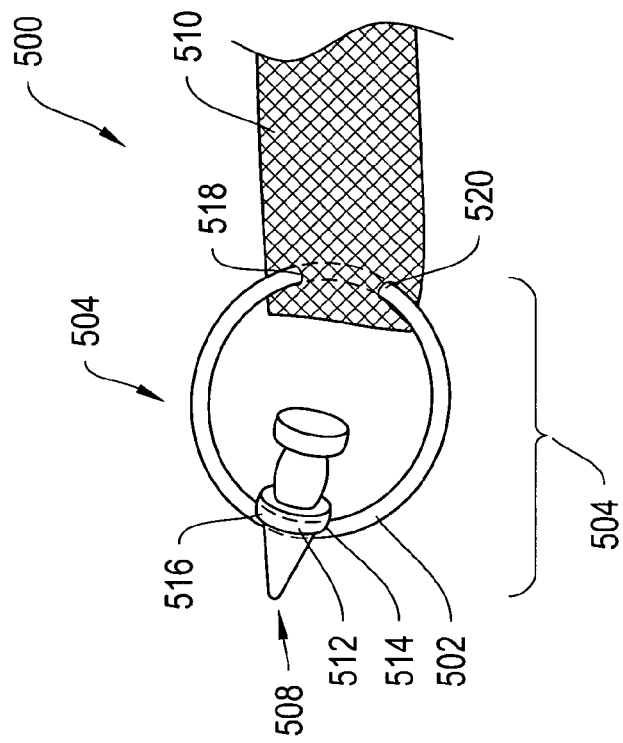
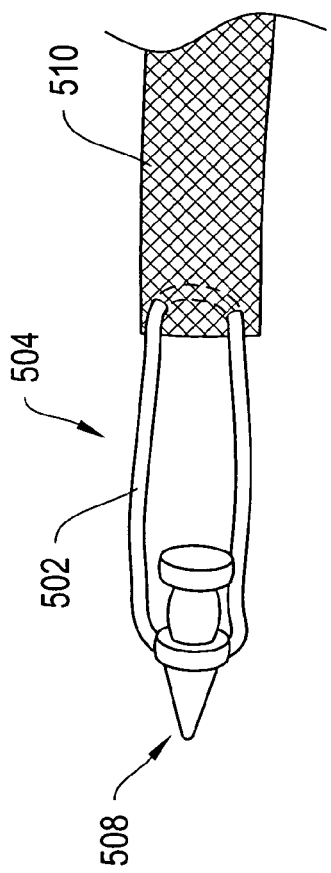
Figure 5A
Figure 5B

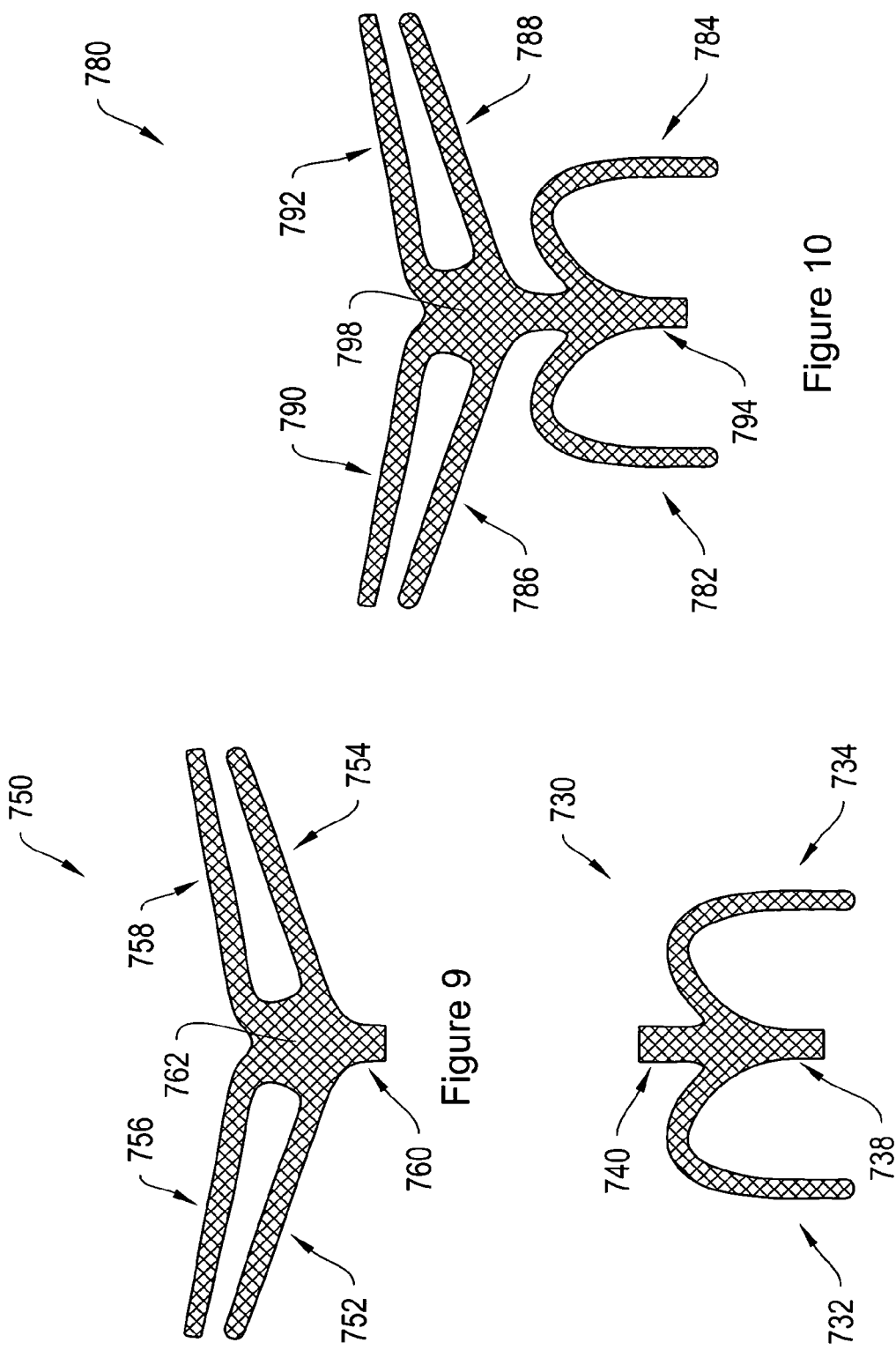

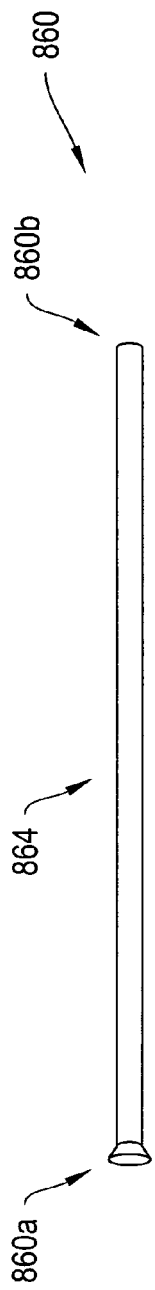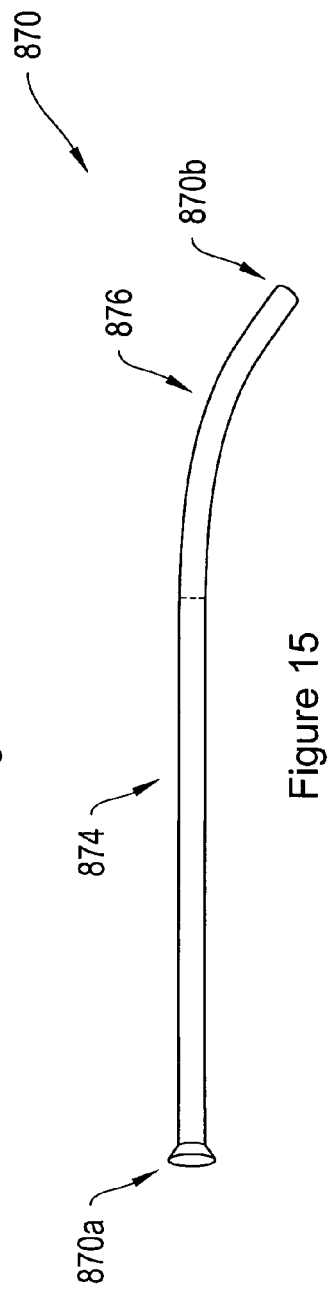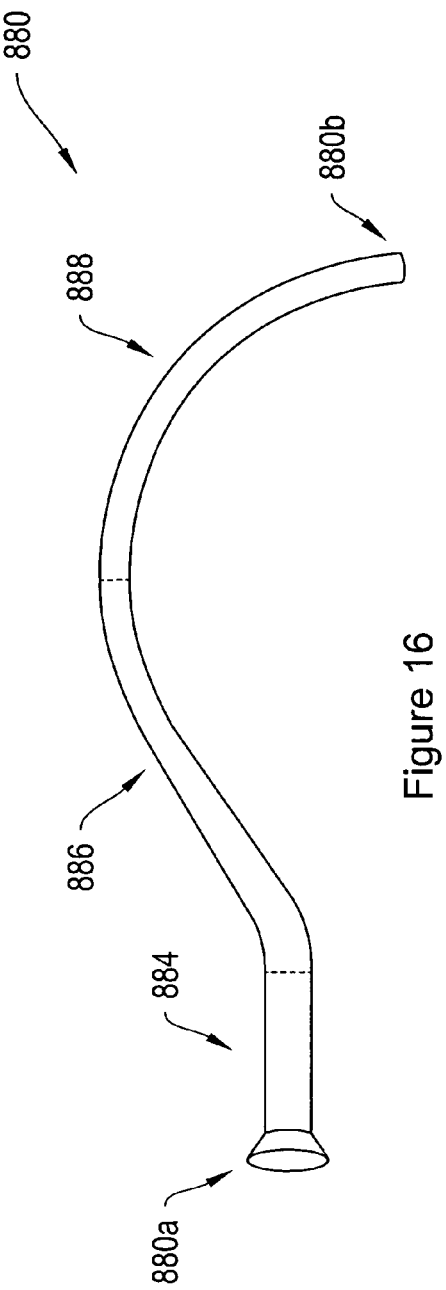

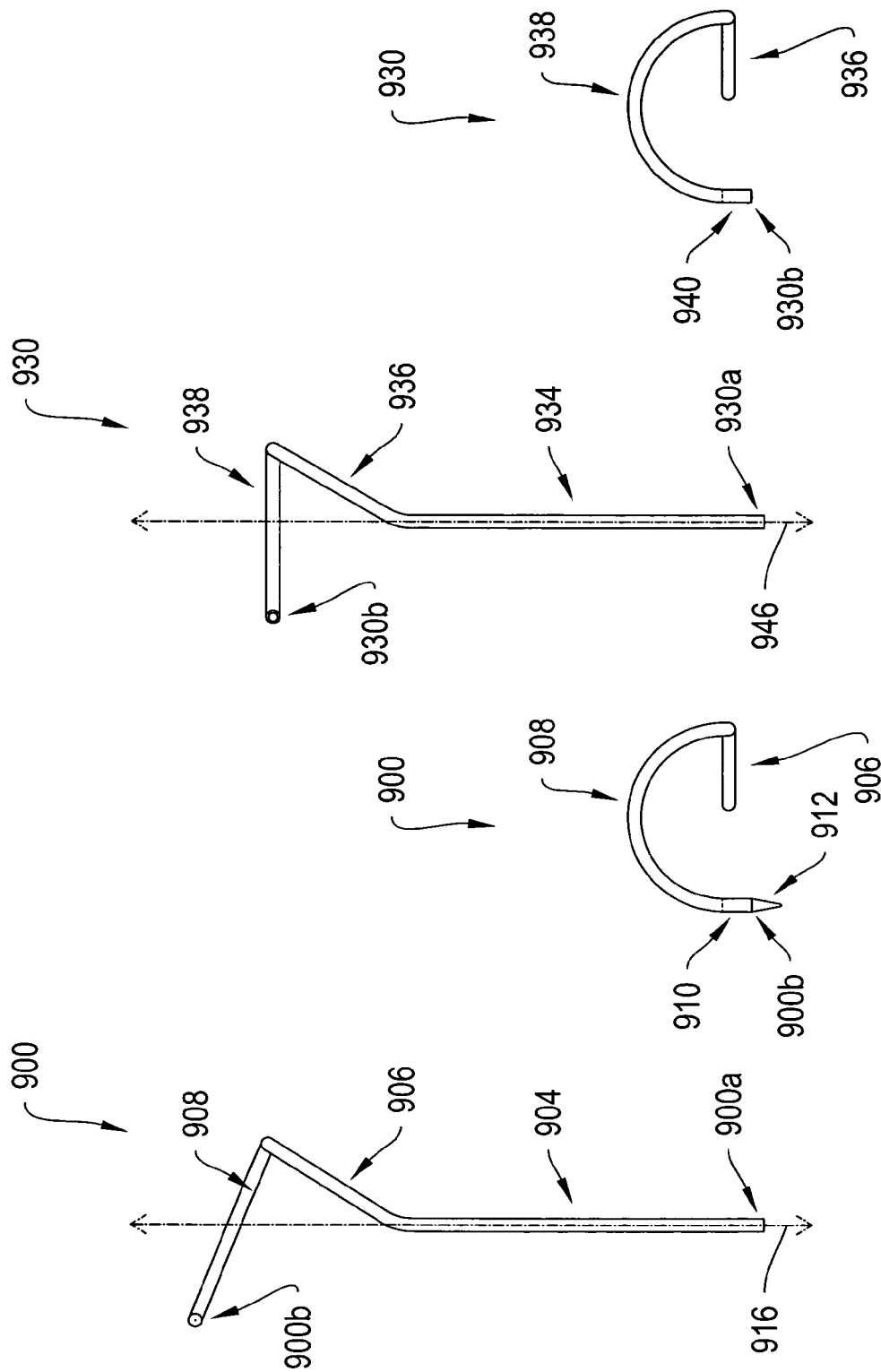

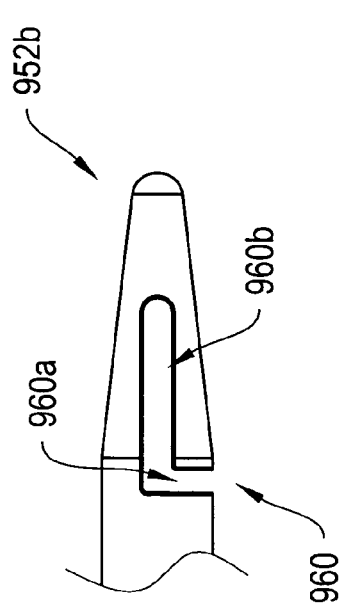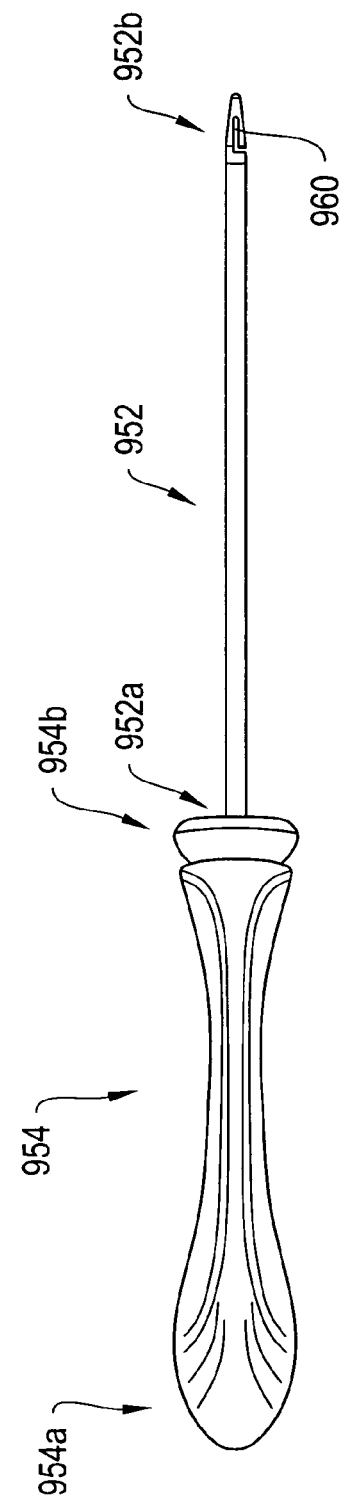

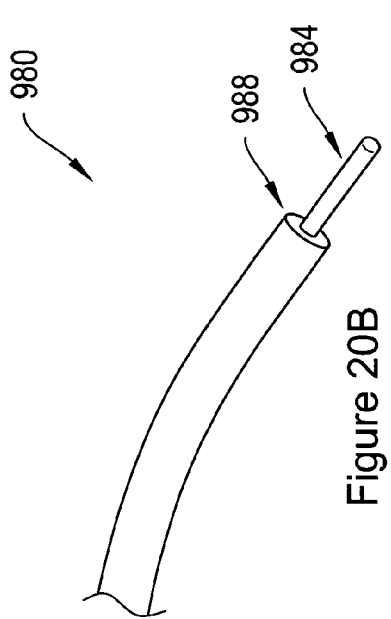
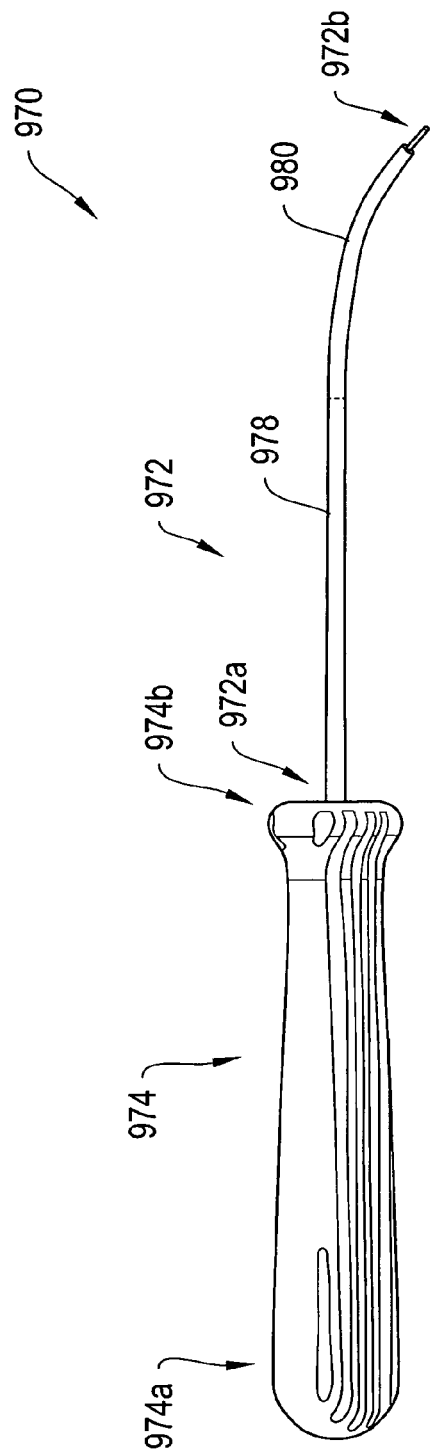
Figure 20B
Figure 20A

PELVIC FLOOR REPAIR SYSTEM

CROSS-REFERENCE TO RELATED APPLICATIONS

This application claims the benefit of U.S. Provisional Application Nos. 60/702,539 and 60/702,540, both filed on Jul. 25, 2005, and U.S. Provisional Application No. 60/715,362, filed on Sep. 8, 2005, the contents of which are incorporated by reference herein in their entirety.

BACKGROUND

Pelvic floor disorders afflict many women. According to some studies, about 1 out of 11 women need surgery for a pelvic floor disorder during her lifetime. The pelvic floor generally includes muscles, ligaments, and tissues that collectively act to support anatomical structures of the pelvic region, including the uterus, the rectum, the bladder, and the vagina. Pelvic floor disorders include vaginal prolapse, vaginal hernia, cystocele, rectocele, and enterocele. Such disorders are characterized in that the muscles, ligaments and/or tissues are damaged, stretched, or otherwise weakened, which causes the pelvic anatomical structures to fall or shift and protrude into each other or other anatomical structures.

Moreover, pelvic floor disorders often cause or exacerbate female urinary incontinence (UI). One type of UI, called stress urinary incontinence (SUI), affects primarily women and is generally caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged, resulting in increases in intra-abdominal pressure (e.g., due to sneezing, coughing, straining, etc.) and consequently the bladder neck and proximal urethra rotate and descend. As a result, the urethra does not close with sufficient response time, and urine leaks through the urethra.

UI and pelvic floor disorders, which are usually accompanied by significant pain and discomfort, are typically treated by implanting a supportive sling in or near the pelvic floor region to support the fallen or shifted anatomical structures or to, more generally, strengthen the pelvic region by, for example, promoting tissue ingrowth. Often, treatments of stress incontinence are made without treating the pelvic floor disorders at all, potentially leading to an early recurrence of the pelvic floor disorder.

Existing devices, methods, and kits for treatment typically apply delivery devices to position a supportive sling into a desired position in the pelvic region by pushing or pulling the sling through the surrounding tissue. When treating pelvic floor disorders and UI it is often desirable to use a tanged mesh implant material, or to use an implant with anchoring projections along an edge of the material. The tangs and projections may irritate the tissue if rubbed against it during implantation. Furthermore, the tangs of the implant may make it difficult to adjust the positioning or tension of the implant during delivery. If the implant is protected by a sleeve during delivery, extra steps are needed to separate the sleeve from the implant and remove it from the body. Accordingly, medical operators and patients need improved systems, methods, and surgical kits for the treatment of pelvic floor disorders and/or urinary incontinence with minimal irritation of the patient's tissue.

SUMMARY OF THE INVENTION

The invention addresses the deficiencies of the prior art by providing an improved implant delivery system. More particularly, in various aspects, the invention provides an implant with an attachment strap and a sheath for use in delivering the implant to patient tissue.

In one aspect, the invention provides a system for delivering an implant to a patient for the treatment of pelvic floor disorders such as cystocele, rectocele, vaginal prolapse, and other similar disorders. An exemplary system includes an implant having an attachment strap, an end termination member attached to the strap, and one or more soft tissue anchors attached to the implant. The system also includes a shaft having a slot located at a distal end for associating with the end termination member of the implant, and a sheath having a hollow center adapted to allow the shaft to extend therethrough.

According to one implementation, the slot in the shaft is L-shaped. In various configurations, the exemplary system further includes a handle coupled to the shaft. The system may also include a handle coupled to the sheath. According to one feature, the handle is removable.

According to various implementations, the one or more soft tissue anchors includes one or more tangs on the implant strap. In other implementations, the end termination member may be one or more of the soft tissue anchor(s). The end termination member may be a loop or a ring. The end termination member may have at least one radially extending leg, and may have two radially extending legs.

In various configurations, at least one of the shaft and the sheath is substantially straight, or at least one of the shaft and the sheath has a curved shape. According to one embodiment, the shaft is rigid and the sheath is flexible. According to another embodiment, the sheath is rigid and the shaft is flexible. In one implementation, the sheath is curved and the shaft is flexible material, and the shaft bends to extend through the center of the sheath upon insertion.

According to one configuration, the shaft is longer than the sheath. According to another configuration, a tip is attached to a distal end of the sheath.

According to one implementation, the implant has two arms and a posterior extension portion and is adapted to be positioned under a posterior pelvic region. The two arms may arch in a posterior direction, toward the posterior pelvic region.

According to another implementation, the implant has four arms and is adapted to be positioned under an anterior pelvic region. The arms may extend laterally from the center of the implant and in an anterior direction, toward the anterior pelvic region.

According to a further implementation, the implant has six arms and is adapted to be positioned under the pelvic region. Two of the arms may arch in a posterior direction, toward the posterior pelvic region, and four of the arms may extend laterally from the center of the implant and in an anterior direction, toward the anterior pelvic region.

In various implementations, the implant has a tanged first edge. The implant may include a pattern of projections.

According to one aspect, the invention also provides a method for delivering an implant to a patient including inserting a sheath having a hollow center into an incision in the patient, inserting a shaft of a delivery device into the center of the sheath, associating an end termination member of the implant with the slot, advancing the shaft and the associated implant through the sheath, and anchoring the implant in the patient's pelvic floor region.

In one implementation, the shaft pulls the end termination member through the sheath. In another implementation, the shaft pushes the end termination member through the sheath. The shaft may be advanced into the sheath prior to advancing the sheath into the incision. According to one feature, the end termination member is removed from the implant after it has been advanced through the sheath.

According to one implementation, the shaft is advanced into the sheath prior to advancing the sheath into the incision. Following insertion of the sheath in the patient, the shaft may be removed from the sheath, pulling the end termination member through the sheath. An arm of the implant may also be pulled through the sheath. The sheath may be removed from the patient, leaving the implant anchored in patient tissue. In one embodiment, the implant is anchored in patient tissue through one or more tangs on the implant. In another embodiment, the end termination member anchors in patient tissue.

According to another implementation, the sheath is inserted through the patient's gluteus maximus. The sheath may also be inserted through the sacrospinous ligament.

Other aspects and advantages of the invention are described below with respect to various illustrative embodiments.

BRIEF DESCRIPTION OF THE DRAWINGS

Various illustrative embodiments of the invention are described below with reference to the appended drawings, which may not be drawn to scale and in which like parts are designated by like reference designations. These depicted embodiments are to be understood as illustrative of the invention and not as limiting in any way.

FIG. 5A shows an implant assembly including an end termination member comprising a ring and a dilator, attached to the arm of a mesh implant.

FIG. 5B shows an implant assembly including an end termination member comprising an elastic ring and a dilator, attached to the arm of a mesh implant.

FIG. 8 shows a mesh implant including two arms and a tail, and adapted to be positioned under a posterior pelvic region.

FIG. 9 shows a mesh implant including four arms and a tail, and adapted to be positioned under an anterior pelvic region.

FIG. 10 shows a mesh implant including six arms and a tail, and adapted to be positioned under the pelvic region.

FIG. 14 is a side-view of a straight sheath for use in delivering an implant to patient tissue.

FIG. 15 is a side-view of a sheath with a curved distal end, for use in delivering an implant to patient tissue.

FIG. 16 is a side-view of a curved sheath for use in delivering an implant to patient tissue.

FIG. 17A is a side-view of a sheath with a spiral-shaped distal end for use in delivering an implant to patient tissue.

FIG. 17B is a top-view of the sheath of FIG. 17A.

FIG. 18A is a side-view of an alternative sheath with a spiral-shaped distal end for use in delivering an implant to patient tissue.

FIG. 18B is a top-view of the sheath of FIG. 18A.

FIG. 19A is a side-view of a delivery device comprising a handle and a straight shaft, with an L-slot on the distal end of the shaft.

FIG. 19B shows an enlarged view of the L-slot on the distal end of the delivery device shown in FIG. 19A.

FIG. 20A is a side-view of a delivery device comprising a handle and a shaft with a curved distal end, and a reduced-diameter tip portion at the distal end.

FIG. 20B shows an enlarged view of the reduced-diameter tip-portion of the delivery device shown in FIG. 20A.

DESCRIPTION OF ILLUSTRATIVE EMBODIMENTS

As described in summary above, the invention, in one illustrative embodiment, relates to systems and methods for delivering and placing a medical implant at an anatomical site in the body of a mammal. In particular, in various illustrative examples, the invention provides delivery devices, systems, and methods for placing an implant, e.g., a pelvic floor support mesh. In one aspect, the implant includes a supportive pelvic floor mesh having end termination members, which act as soft tissue anchors, for use in sling delivery. The implant is delivered to the pelvic floor region, which may include the periurethral and other retropubic tissue. Delivery approaches may include a transobturator approach (inside-out or outside-in), a suprapubic approach, a pre-pubic approach, a retropubic approach, a transabdominal approach, and any combination of approaches. In one embodiment, the system includes a sheath having a hollow center and a delivery device having a shaft. The shaft may be inserted through the sheath, attached to an end termination member, and used to advance the end termination member and the associated implant through the sheath. The patient may be either a female patient or a male patient.

Figure 1:
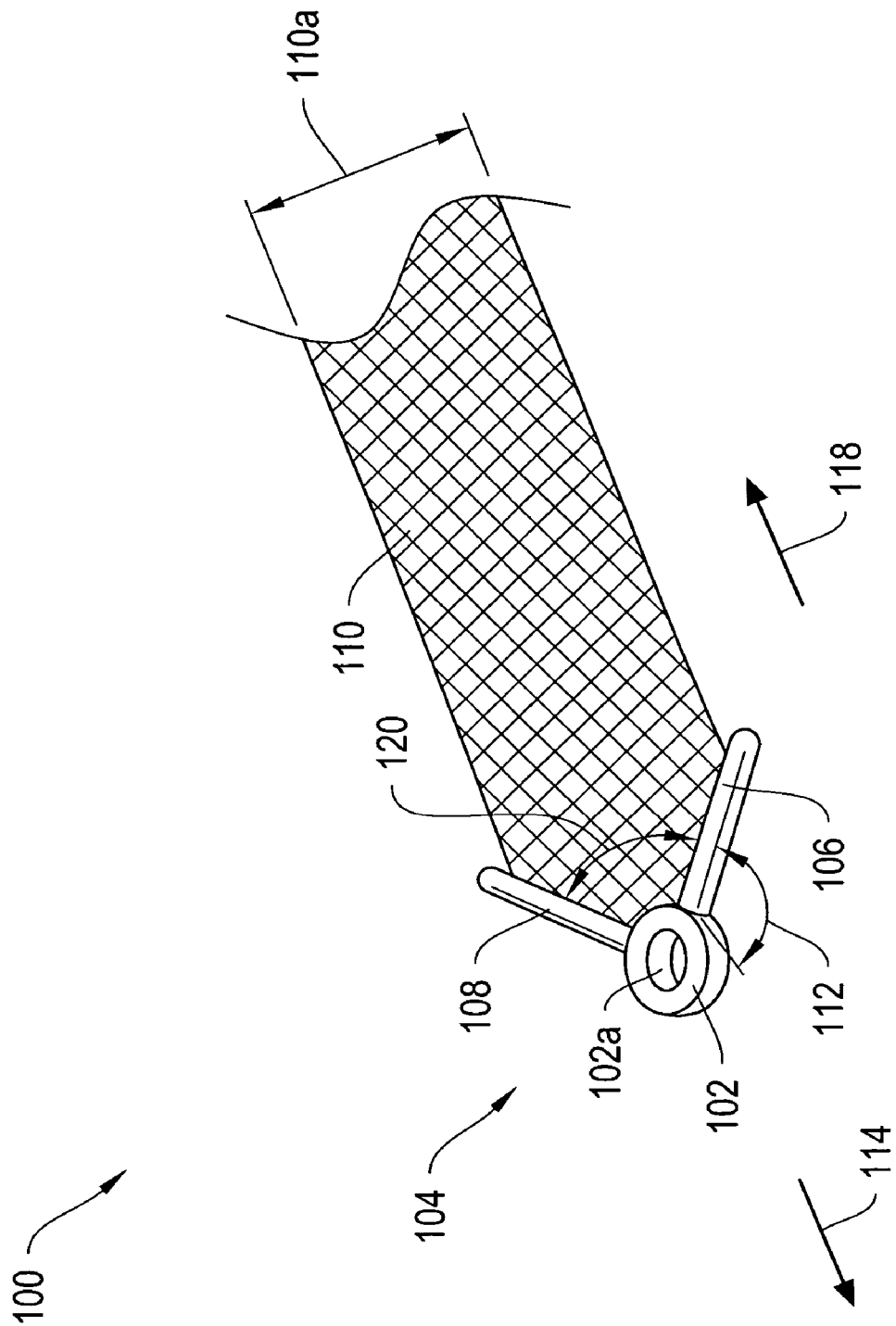
FIG. 1 shows a sling assembly including an implant end termination member comprising a ring and two legs, attached to the arm of a mesh implant.

More particularly, FIG. 1 shows a sling assembly 100 including an exemplary implant end termination member 104 attached to the arm of a mesh implant 110. The end termination member 104 includes a ring 102, a first arm 106, and a second arm 108. The arms 106 and 108 extend radially from the ring 102. In one embodiment, the end termination member 104 is a soft tissue anchor. The ring 102 may be sized and shaped to engage with a delivery device, such as, without limitation, the distal end of a shaft or needle of the delivery devices 950, 970, and 1000 described below with respect to FIGS. 19A-19B, 20A-20B, and 21.

According to one embodiment, in operation, an operator couples the ring 102 to a slot in the shaft of a delivery device, such as the L-slot 960 of FIG. 19B, for implantation into a patient, as will be discussed in further detail below with respect to FIGS. 19A and 19B. According to another embodiment, in operation, an operator places the ring 102 over the tip of a delivery device shaft and slides the ring 102 down the tip until the ring 102 abuts against a step, shoulder, or other stopping mechanism, as will be discussed in further detail below with respect to FIGS. 20A and 20B. The ring 102 includes an inner surface 102a that, in certain embodiments, is tapered to inter-fit with the tip of a delivery device.

According to one embodiment, the ring 102 and arms 106 and 108 of the end termination member 104 are coplanar with the implant 110. As a result, the implant assembly 100 has a low delivery profile. The delivery profile refers to the maximum cross-sectional area of a passageway through the patient's anatomy that is required for placement of the implant, and smaller delivery profiles may be beneficial at least in part because they may reduce tissue damage during implant delivery. According to another embodiment, the end termination member 104 is flexible, such that the ring 102 and arms 106 and 108 may be arranged in a non-coplanar position.

The ring 102 may be any shape, including square, triangular, oval, or other preferred shapes. The ring 102 may also be any size, and in particular may be configured to couple with shafts or needles of varying dimensions.

The arms 106 and 108 may be sized and shaped to engage with and attach to the implant 110. The arms 106 and 108 of the end termination member 104 extend radially from the ring 102 and adjoin at an angle 112, forming a V-shape. In certain embodiments, the end termination member 104 is flexible such that the angle 112 can be increased or decreased upon application of appropriate mechanical pressure. Similarly, the angle 120 formed between the arms 106 and 108 may also vary. For example, the arm 106 and 108 may be squeezed together, reducing the angle 120 to about zero degrees. By way of example, if the implant assembly 100 passes through tissue or through a sheath in a forward direction 114, the arms 106 and 108 interact with the tissue or with the sides of the sheath to increase the angle 112 and decrease the angle 120, as the arms 106 and 108 are pushed together. If the implant assembly 100 passes through tissue in a retrograde direction 118, the arms 106 and 108 may interact with the tissue to decrease the angle 112 and increase the angle 120, as the arms 106 and 108 are pushed apart. The varying angles 112 and 120 facilitate movement of the implant assembly 100 in the forward direction 114, and impedes movement of the mesh strap 110 in the retrograde direction 118. In certain embodiments, the angle 112 may vary from between about 0 degrees to about 90 degrees, and in other embodiments, the angle 112 may vary to more than about 90 degrees. Similarly, in various embodiments, the angle 120 may vary from between about 0 degrees to about 110 degrees, and in other embodiments, the angle 120 may vary to more than about 110 degrees. In one embodiment, the flexibility of the end termination member 104 may vary. The flexibility of the end termination 104 and the measurement of the angles 112 and 120 are generally chosen to suit the particular delivery path and location for anchoring the implant, as well as the condition being treated.

According to an additional embodiment, the V-shaped configuration of the arms 106 and 108 acts to engage with patient tissue to resist removal once the implant assembly 100 is implanted. The depicted arms 106 and 108 extend beyond the width 110a of the mesh implant 110 to provide additional engagement with tissue, but in other illustrative embodiments, the arms 106 and 108 may have any length, and may not extend beyond the width 110a of the implant 110. In one embodiment, the distance between the arms 106 and 108 is less than the width of the implant 110, such that the arms 106 and 108 do not extend to the edge of the implant 110.

According to one embodiment, the end termination member 104 may be molded to the implant 110, as described in further detail in U.S. patent application "Systems, Devices, and Methods for Treating Pelvic Floor Disorders," Ser. No. 11/400,111, filed Apr. 6, 2006, which is incorporated herein by reference in its entirety. According to a further embodiment, also described in the reference "Systems, Devices, and Methods for Treating Pelvic Floor Disorders," the end termination member 104 may include two pieces: a top piece, and a bottom piece. According to this embodiment, the two pieces may be snapped together to attach the end termination member 104 to the implant 110.

Figure 2:
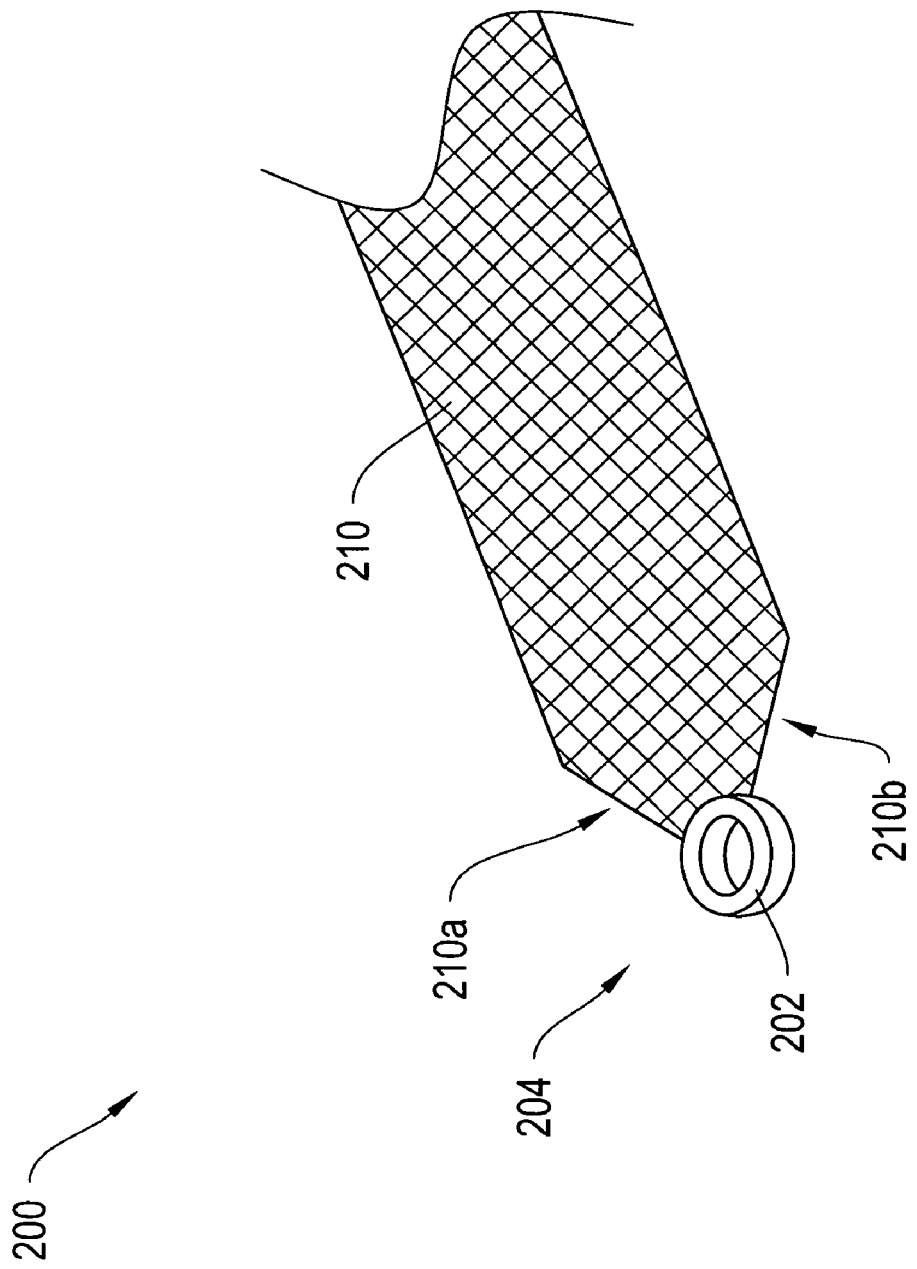
FIG. 2 shows an implant assembly including an end termination member comprising a ring, attached to the arm of a mesh implant.

FIG. 2 shows an implant assembly 200 including an end termination member 204 and a mesh implant 210. The end termination member 204 includes a ring 202, and does not include radially extending legs. A manufacturer may affix the end termination member 204 to the implant 210 using any of the methods described above. In the depicted implant assembly 200, the manufacturer has trimmed corners of the implant 210 at locations 210a and 210b. According to alternative embodiments, the corners of the implant may not be trimmed, or the corners may be trimmed to any suitable shape, including round, triangular, and square.

Figure 3:
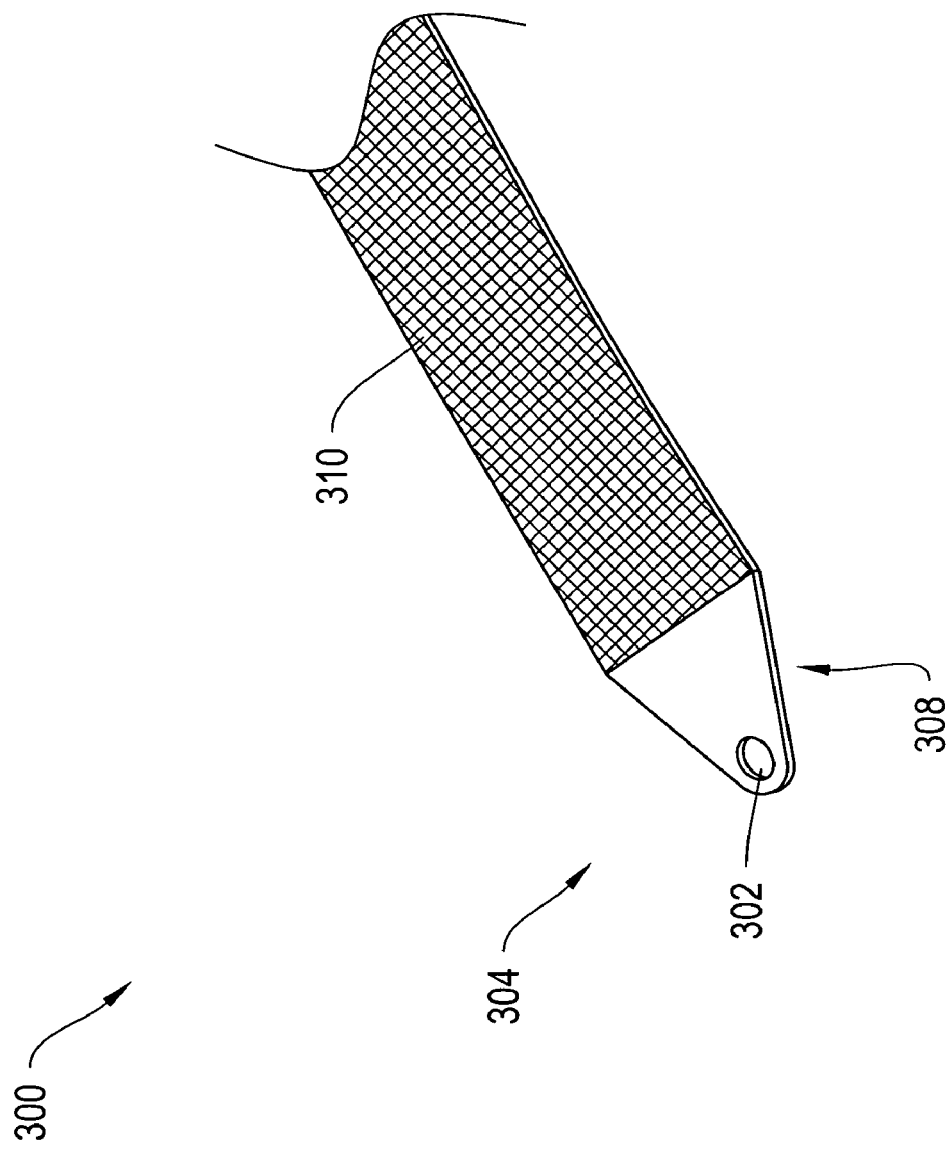
FIG. 3 shows an implant assembly including an end termination member comprising a tab with an aperture, attached to the arm of a mesh implant.

FIG. 3 shows another embodiment of an implant assembly 300 including end termination member 304 and mesh implant 310. The end termination member 304 lies substantially coplanar with the implant 310, and includes a tab-shaped region 308 and an aperture 302. The aperture 302 may be sized and shaped to couple with the shaft of a delivery device. In one embodiment, the aperture 302 is sized, shaped and positioned in the tab region 308 to couple with the slot in the end of the shaft of a delivery device, such as the L-slot 960 shown in FIG. 19B. In one embodiment, the aperture 302 is small (i.e., it has a diameter of less than about 2 mm), and is sized to couple with the narrow needle of a delivery device. In other embodiments, the aperture 302 is sized to allow an operator to thread a filament therethrough. The filament may couple to a separate soft tissue anchor as described in connection with other embodiments herein. In an exemplary manufacturing technique, a manufacturer dips the implant 466 in a curable plastic to form the end termination member 304. The manufacturer then trims the plastic to create the tab shape and punches a hole through the plastic to create the aperture 302. However, in alternative embodiments, the manufacturer may pre-form the end termination member 304 and subsequently snap-fit, glue, stitch, or otherwise attach it to the implant 310. Additional embodiments of the end termination member 304 are described in the above reference "Systems, Devices, and Methods for Treating Pelvic Floor Disorders.".

Figure 4:
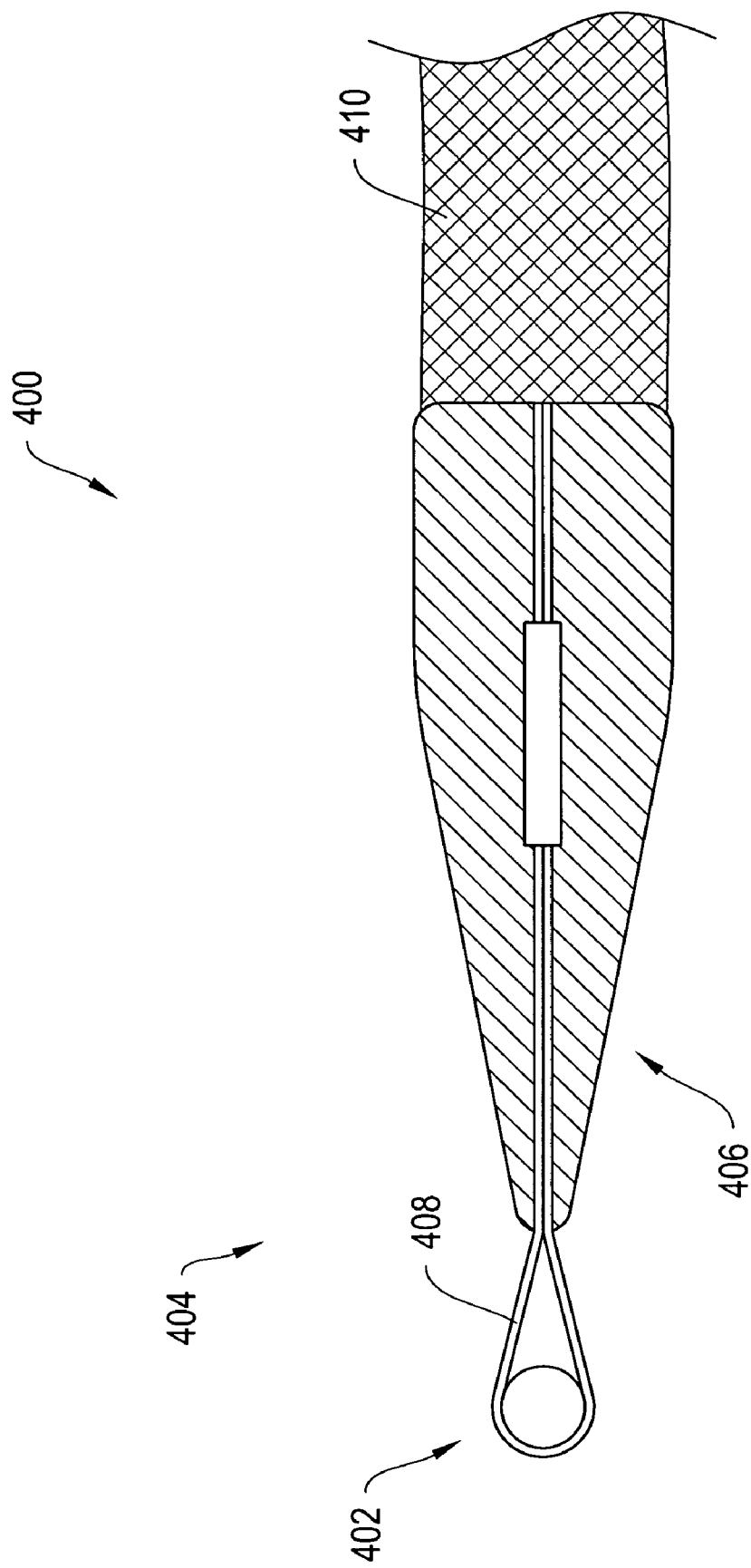
FIG. 4 is a longitudinal cross sectional view of an end termination member comprising an association loop and a dilator, attached to the arm of a mesh implant.

FIG. 4 is a longitudinal cross sectional view of a sling assembly 400 including and end termination member 404 and an implant 410. The end termination member 404 includes an association loop 402 and a dilator 406. According to a preferred embodiment, the dilator 406 is a rigid polymer tube of approximately 2 cm in length terminating in a conical tip. Embedded and secured along the length of the dilator 406 are two ends of a wire 408, which may be formed from twisted metal strands. The wire 408 extends from the conical tip of the dilator 406 to form an association loop 402. According to one embodiment, the association loop 402 extends approximately 15 mm from the end of the conical tip of the dilator 406. According to other embodiments, the association loop extends any suitable distance from the conical tip of the dilator 406, including about 5 mm, about 10 mm, about 20 mm, about 25 mm, about 30 mm, about 35 mm, about 40 mm, about 50 mm, about 75 mm, about 1 cm, and more than 1 cm. The association loop 402 is preferably deformable, but generally shape-retaining. Thus, according to one embodiment, the shape of the association loop 402 may be changed by outside pressure, but the association loop 402 will return to its original shape upon release of the outside pressure.

According to one embodiment, the association loop 402 of the end termination member 404 is sized and shaped for coupling to a slot in the end of a shaft of a delivery device, such as the L-slot 960 of delivery device 950 shown in FIGS. 19A and 19B.

FIG. 5A shows an implant assembly 500, including an end termination member 504 and a mesh implant 510. The end termination member 504 includes a ring 502 and a dilator 508. The dilator 508 may also act as a soft tissue anchor. According to one embodiment, the ring 502 threads through apertures 514 and 516 in a first shoulder region 512 of the dilator 508. More particularly, the ring 502 couples with dilator 508 by threading through apertures 514 and 516, and couples with the mesh implant 510 by threading through apertures 518 and 520 in the mesh implant 510. According to one embodiment, the ring 502 is constructed of a rigid or semi-rigid material, and maintains its shape. In another embodiment, the ring 502 is constructed of a deformable material that is shape retaining.

In an alternative embodiment, as shown in FIG. 5B, the ring 502 is flexible, and may be constructed from an elastic material. In this embodiment, the ring 502 stretches to absorb lateral stresses. Woven surgical implants may stretch and damage due to stresses during delivery of the implant, and stretching of the ring 502 may help prevent stretching and damage to the implant 510 during delivery. Additionally, elastic rings adjust to short term and/or long term changes in the patient's changing anatomy to prevent damage to the surgical implant 510. For example, when the patient sneezes, coughs, or jumps, muscles in the pelvic region can contract and anatomical structures may shift. Anatomical structures may also shift over long periods of time because of the patient's changing anatomy due to, for example, weight gain or weight loss. In such cases, elastic rings stretch to absorb the stresses caused by these short-term and long-term changes, thereby preventing the changes from damaging the surgical implant 510.

According to various embodiments, the ring 502 is sized and shaped to couple with the shaft of a delivery device. In one embodiment, the ring 502 couples with a slot in the end of the shaft of a delivery device, such as the L-slot 960 of delivery device 950 shown in FIGS. 19A and 19B.

Figure 6:
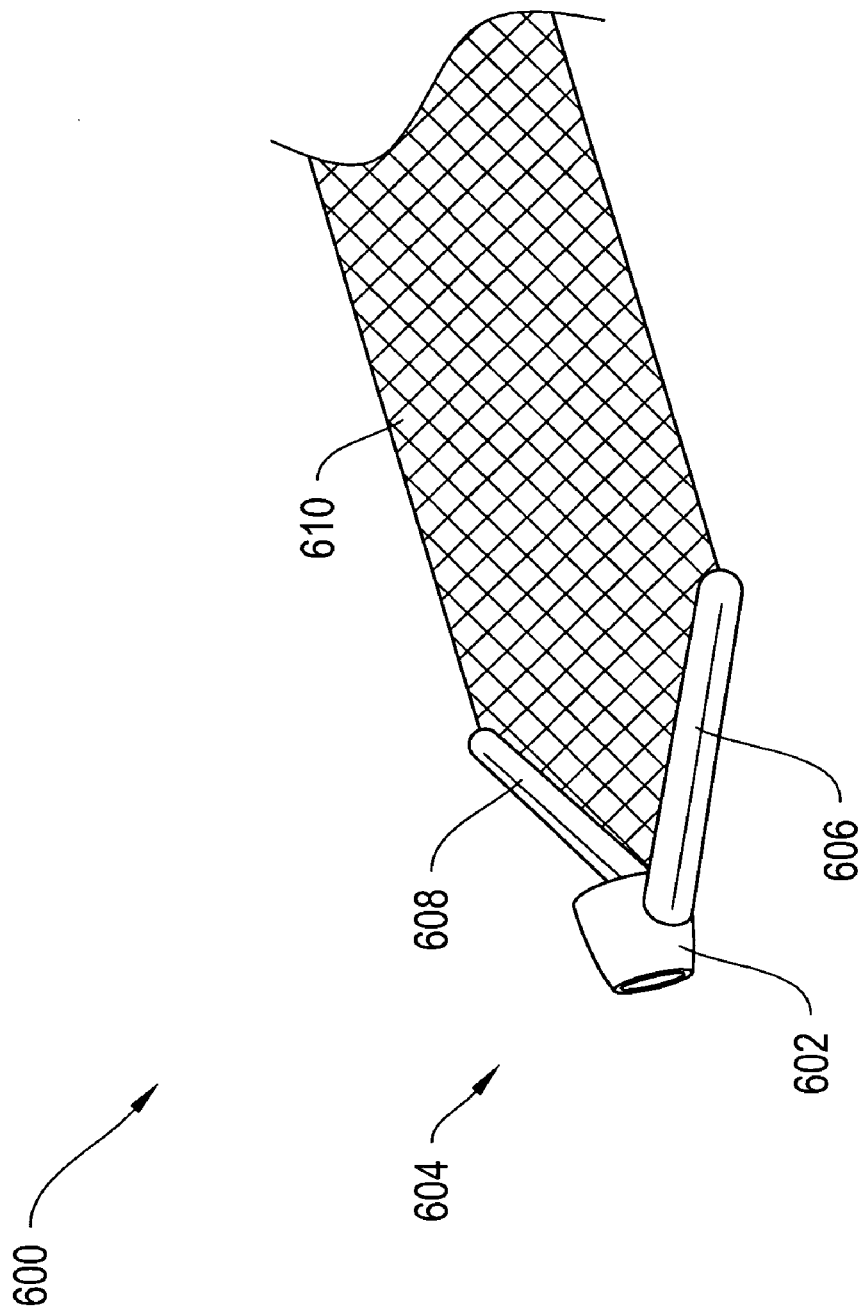
FIG. 6 shows an implant assembly including an end termination member including a cylindrical ring and two legs, attached to the arm of a mesh implant.

FIG. 6 shows an implant assembly 600 including an end termination member 604 and a mesh strap 610. The end termination member 604 includes arms 606 and 608 and a ring 602 that has a circular cross-section lying in a plane that is perpendicular to a plane of the mesh strap. According to various embodiments, the end termination member 604 couples to the end of the shaft of a delivery device, such as the delivery device 970 described below with respect to FIGS. 20A and 20B. The orientation of the ring 602 with respect to the end termination member 604, as compared with the ring 102 with respect to the end termination member 104 of FIG. 1, results in a different orientation of the mesh implant 610 with respect to the delivery device when the mesh implant and the device are coupled. This alternative orientation results in the implant 610 aligning with the tip of the shaft, as opposed to extending from the shaft tip at about a 90 degree angle. The alternative orientation using end termination member 604 may be preferred by a medical operator when the operator is delivering the mesh implant 610 through a narrow anatomical incision, through a narrow pathway in a patient's anatomy, and/or through a sheath.

Other exemplary alternatives to the end termination members 104, 204, 304, 404, 504, and 604 are disclosed in U.S. patent application Ser. No. 10/542,365 and U.S. patent application Ser. No. 11/152,898, the contents of which are incorporated by reference herein in their entirety.

Figure 7:
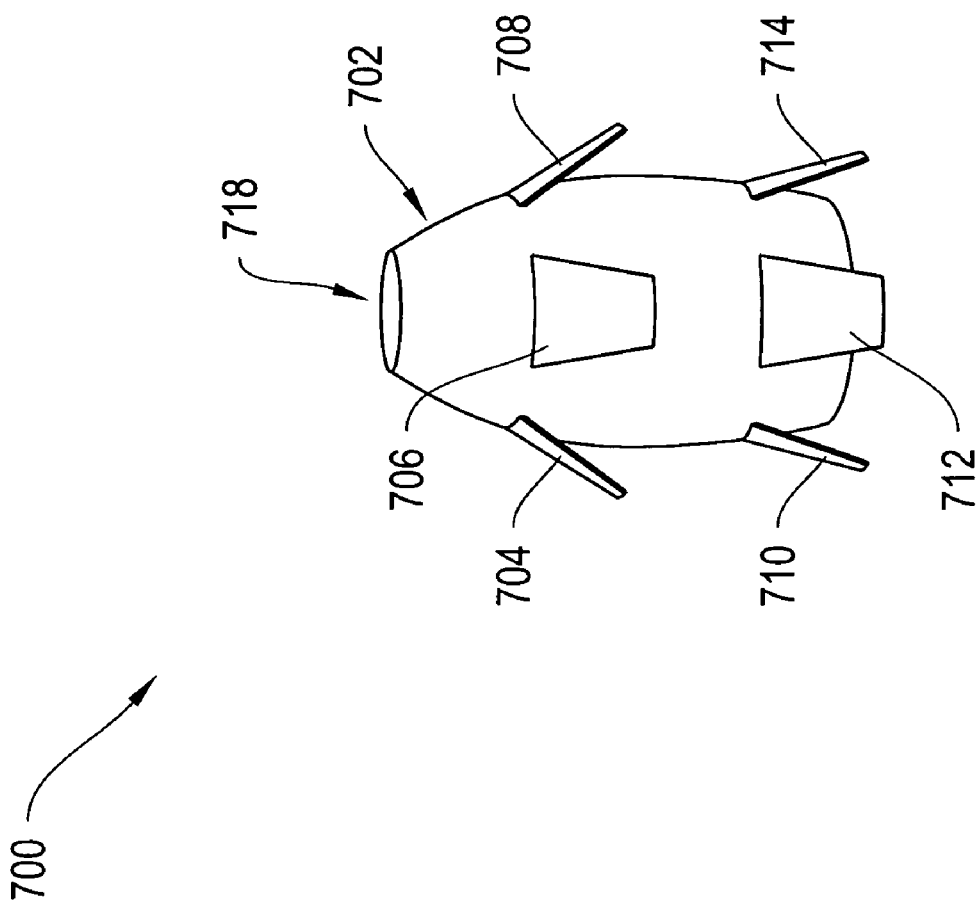
FIG. 7 shows a soft tissue anchor 700.

FIG. 7 shows a soft tissue anchor 700, which may be attached to the arm of an implant, such as implants 730, 750, and 780 shown in FIGS. 8, 9, and 10, and described below. The soft tissue anchor 700 includes a center portion 702, and tabbed projections 704, 706, 708, 710, 712, and 714. Additional projections may be present on the reverse side (not shown) of the anchor 700. The center portion 702 of the anchor 700 may be solid or hollow. In one embodiment, the center portion 702 includes a through-aperture 718. The soft tissue anchor 702 may be adapted to interfit with the shaft of a delivery device, such as the shaft 972 of the delivery device 970, shown in FIGS. 20A and 20B, and discussed below.

FIG. 8 shows a mesh implant 730 including two arms 732 and 734, and a posterior extension portion 738. According to one embodiment, the implant 730 is adapted to be positioned under a posterior pelvic region, and may provide posterior pelvic floor support. According to the illustrative embodiment, the two arms arch in a posterior direction, toward the posterior pelvic region. The mesh implant 730 may also include an anteriorly extending portion 740. According to one embodiment, any of the end termination members 104, 204, 304, 404, 504, and 604 may be attached to the arms 732 and 734 of the implant 730. According to a further embodiment, any of the end termination members 104, 204, 304, 404, 504 and 604 may be attached to the posterior extension portion 738. According to another embodiment, a combination of various end termination members may be used. In yet another embodiment, the arms 732 and 734 may be tanged, similar to the arms 840a and 840b of FIG. 12.

FIG. 9 shows a mesh implant 750 including four arms 752, 754, 756, and 758 and a posterior extension portion 760. According to one embodiment, the implant 750 is adapted to be positioned under an anterior pelvic region, and may provide anterior pelvic floor support. According to another embodiment, the arms 752, 754, 756, and 758 extend laterally from the center 762 of the implant 750 and in an anterior direction, toward the anterior pelvic region. According to one embodiment, any of the end termination members 104, 204, 304, 404, 504, and 604 may be attached to the arms 752, 754, 756, and 758 of the implant 750. According to a further embodiment, a combination of various end termination members may be used. In yet another embodiment, the arms 752, 754, 756, and 758 may be tanged, similar to the arms 840a and 840b of FIG. 12.

FIG. 10 shows a mesh implant 780 including six arms 782, 784, 786, 788, 790, and 792 and a tail 794. According to one embodiment, the implant 780 is adapted to be positioned under the pelvic region, and may provide pelvic floor support. According to another embodiment, two arms 782 and 784 of the implant 780 arch in a posterior direction, toward the posterior pelvic region, while four arms 786, 788, 790, and 792 extend laterally from the center 798 of the implant and in an anterior direction, toward the anterior pelvic region. According to one embodiment, any of the end termination members 104, 204, 304, 404, 504, and 604 may be attached to the arms 782, 784, 786, 788, 790, and 792 of the implant 780. According to a further embodiment, a combination of the various end termination members may be used. In yet another embodiment, the arms 782, 784, 786, 788, 790, and 792 may be tanged, similar to the arms 840a and 840b of FIG. 12.

Figure 11:
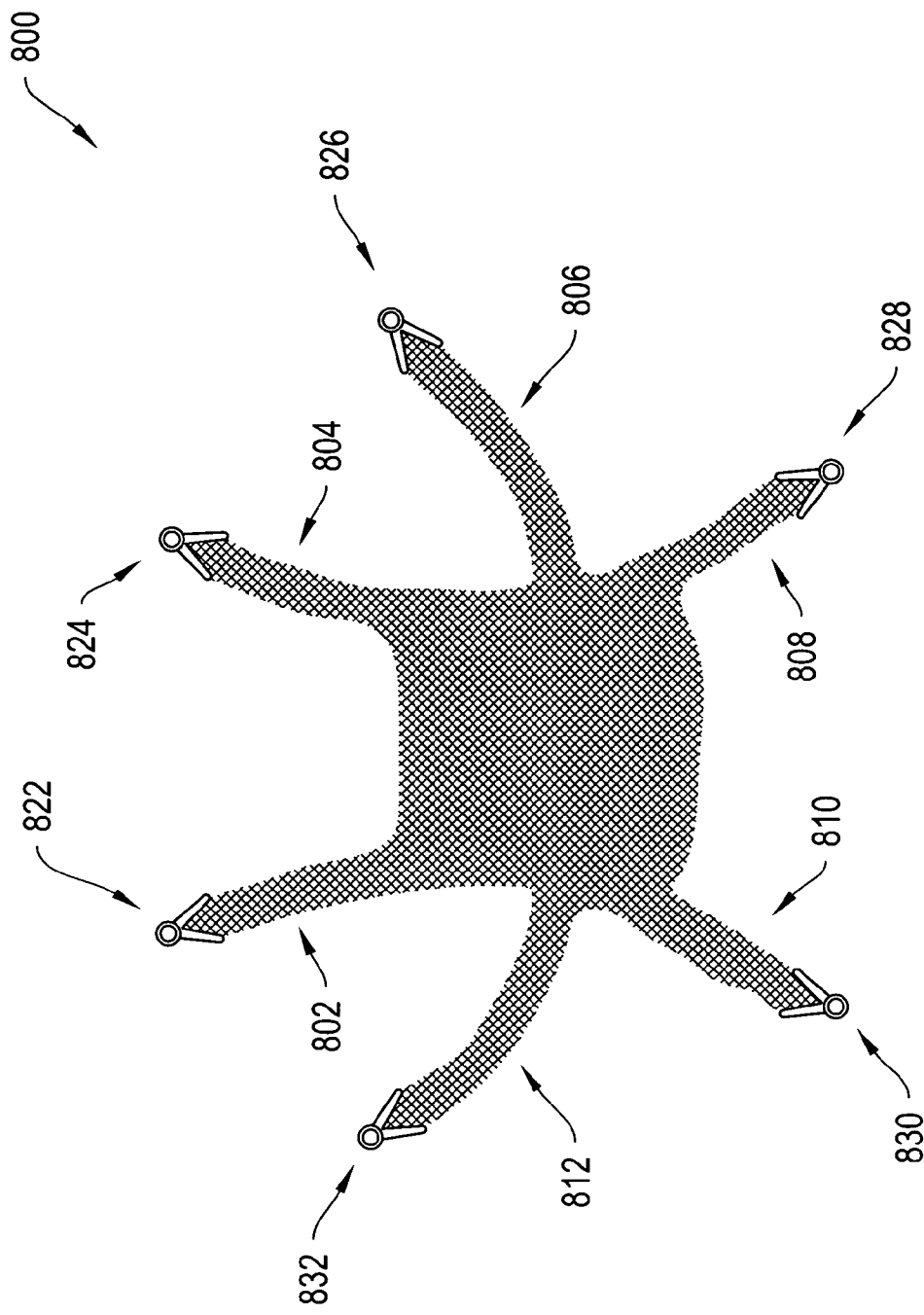
FIG. 11 shows a mesh implant including six arms having end termination members.

FIG. 11 shows a mesh implant 800 including six arms 802, 804, 806, 808, 810, and 812, having end termination members 822, 824, 826, 828, 830, and 832, respectively. While the end termination members 822, 824, 826, 828, 830, and 832 are depicted as being similar to the end termination member 104 of FIG. 1, the end termination members 822, 824, 826, 828, 830, and 832 may include any of the end termination members 104, 204, 304, 404, 504, and 604, or any combination of end termination members 104, 204, 304, 404, 504, and 604.

Figure 12:
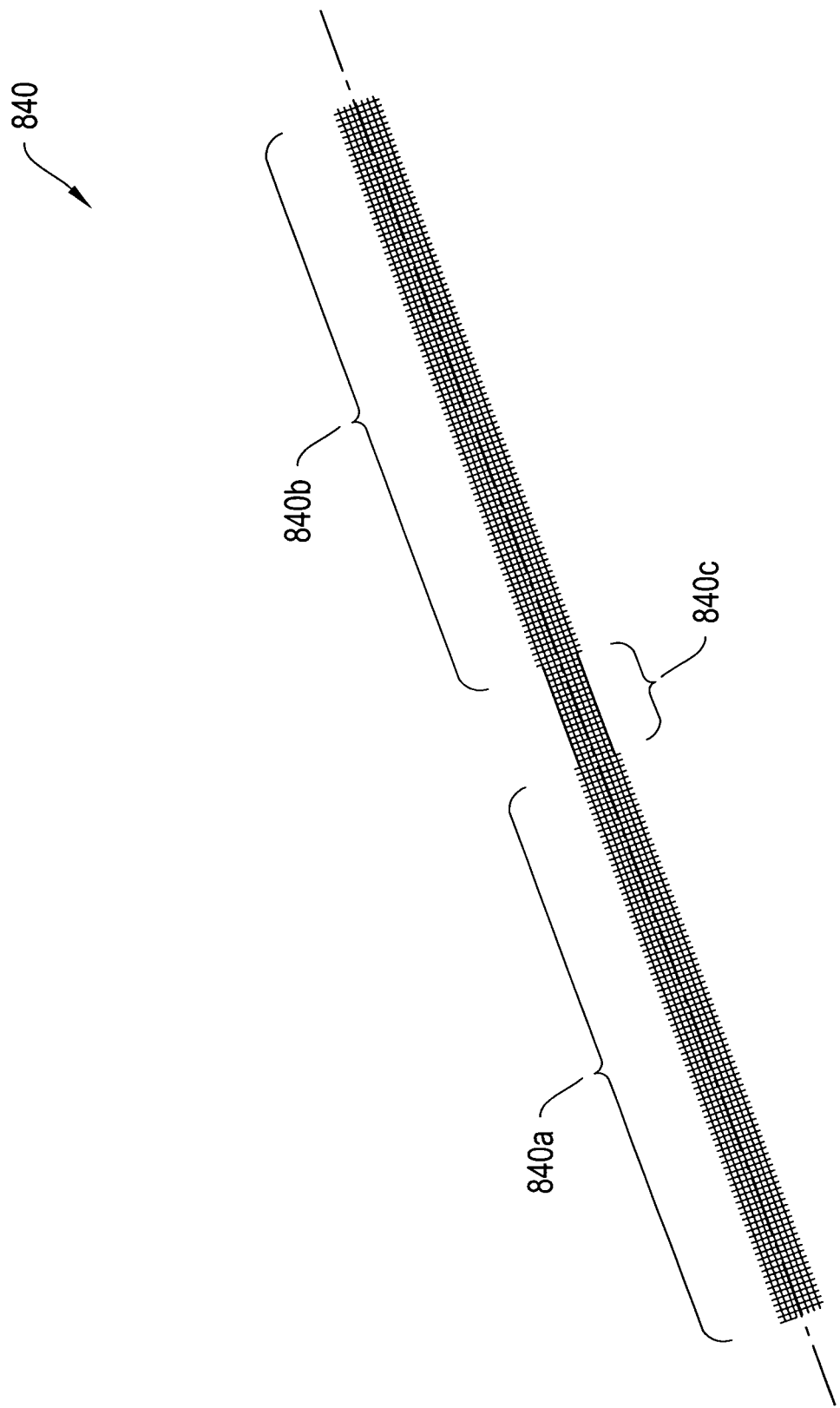
FIG. 12 shows a mesh implant having two tanged end portions and a non-tanged center portion.

FIG. 12 shows an exemplary mesh implant 840 having two end portions 840a and 840b and a center portion 840c. As shown in FIG. 12, the end portions 840a and 840b have tanged edges, which help to anchor the mesh implant following implantation. The center portion 840c has smooth non-tanged edges, which may help prevent irritation of the supported tissue or organ.

Figure 13:
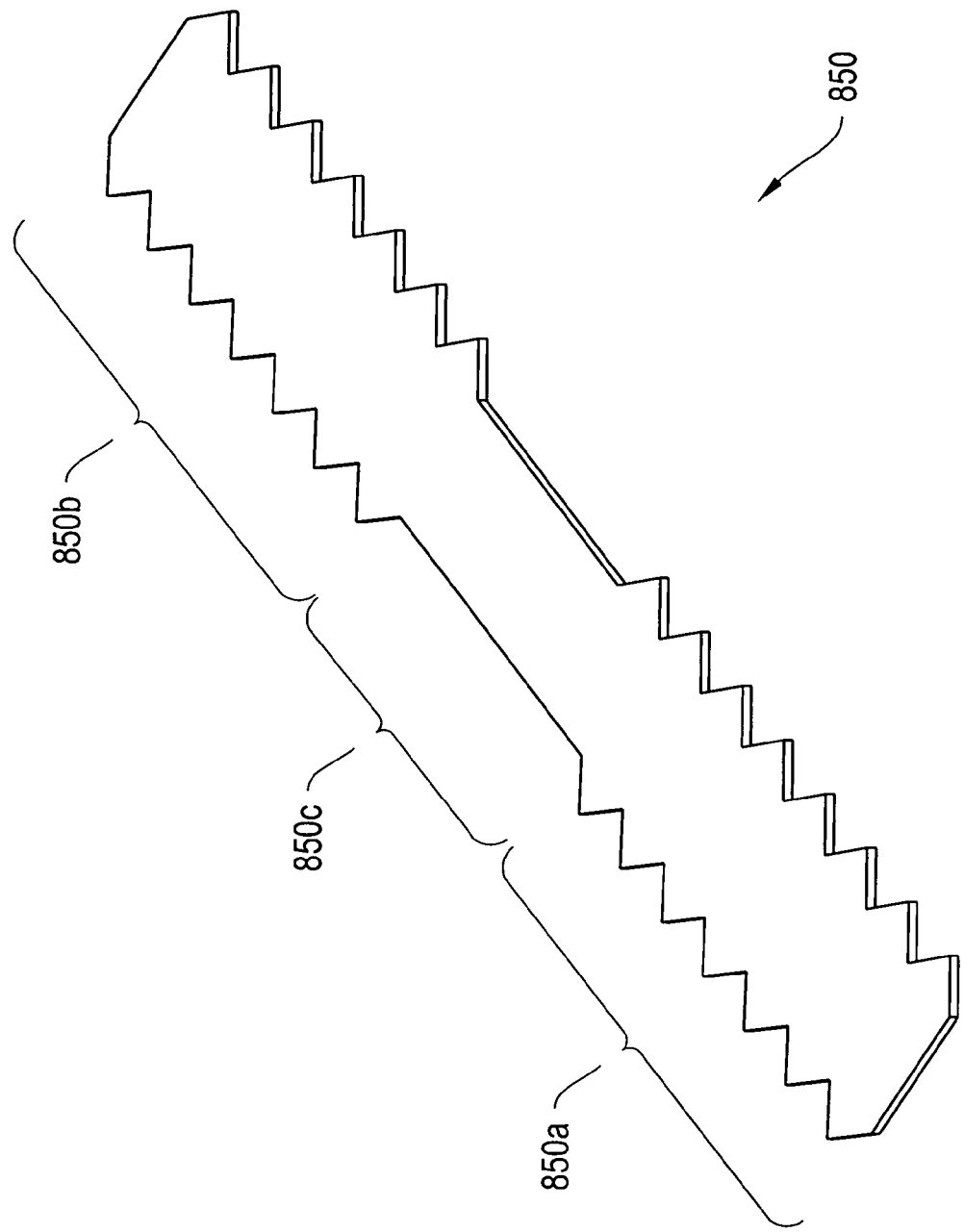
FIG. 13 shows an implant having a center portion and two end portions with a pattern of projections on their lateral edges.

FIG. 13 shows an exemplary implant 850 having two end portions 850a and 850b and a center portion 850c. As shown in the figure, the end portions 850a and 850b comprise a pattern of projections along their lateral edges, which help to anchor the implant in patient tissue upon implantation. The center portion 850c had smooth edges with no projections, which may help prevent irritation of the supported tissue or organ.

According to various embodiments, the arms of an implant are the attachment straps of the implant. According to another embodiment, the attachment straps form a continuum with the center portion of the implant, and may include one or more non-tanged portions.

In one aspect, the implants are inserted into a patient by the use of a sheath. FIGS. 14-16, 17A and 18A are side-views of various exemplary sheathes for such use. According to one embodiment, the sheathes are hollow, to allow for passage of a shaft therethrough. FIG. 14 depicts a sheath 860 having a proximal end 860a, a distal end 860b, and a straight portion 864 extending from the proximal end 860a to the distal end 860b of the sheath 860. FIG. 15 depicts a sheath 870 having a proximal end 870a and a distal end 870b. The sheath 870 includes a straight portion 874 extending from the proximal end 870a of the sheath 870, and a curved portion 876 extending from the straight portion 874 to the distal end 870b of the sheath 870. FIG. 16 depicts a side view of a sheath 880 having a proximal end 880a and a distal end 880b. The sheath 880 includes a straight portion 884 extending from the proximal end of the sheath 880, an upward-curving portion 886, extending from the distal end of the straight portion 884, and a downward-curving portion 888, extending from the distal end of the upward-curving portion 886 to the distal end 880b of the sheath 880. According to one embodiment, the sheathes shown in FIGS. 14-16 all lie substantially in one plane.

FIG. 17A depicts a side view of a sheath 900 for use in delivering an implant to patient tissue, while FIG. 17B depicts a top view of the sheath 900. The sheath 900 has a proximal end 900a and a distal end 900b. The sheath 900 includes a first straight portion 904, a second straight portion 906, a curved portion 908, and a third straight portion 910. Optionally, the sheath 900 further includes a removable tip 912. The first straight portion 904 extends distally away from the proximal end 900a of the sheath 900 along a longitudinal axis 916. The second straight portion 906 extends distally from, but at an angle to the first straight portion 904. In the illustrative embodiment, the second straight portion 906 is substantially coplanar in a first plane with the first straight portion 904. The first curved portion 908 of the sheath 900 extends from a distal end of the second straight portion 906 and curves the sheath 900 back toward the axis 916. The third straight portion 910 of the sheath 900 extends from a distal end of the first curved portion 908, as shown in FIG. 17B. The first curved portion 908 and the third straight portion 910 are substantially coplanar with each other in a second plane. As depicted in FIG. 17B, the curved section 908 defines a substantially constant radius curve.

The optional conical tip 912 of the sheath 900 may attach to the distal end 900b of the sheath 900. The conical tip 912 may be configured for percutaneous punctuation and/or advancement through tissue. However, the tip 912 may be blunt or sharp. A blunt tip provides some resistance to unintended penetration through tissue or organ, such as the bladder.

FIG. 18A depicts a side-view of a sheath 930 configured as a variation of the illustrative sheath 900 of FIG. 17A. FIG. 18B depicts a top-view of the sheath 930. The sheath 930 has a proximal end 930a and a distal end 930b. Similar to sheath 900, sheath 930 includes a straight portion 934 extending distally away from the proximal end 930a of the sheath 930 along a longitudinal axis 946, and a second straight portion 936 extending distally from, but at an angle to the first straight portion 934, and substantially coplanar in a first plane with the first straight portion 934. The sheath 930 further includes a first curved portion 938 extending from a distal end of the second straight portion 936 and curving the sheath 930 back toward the axis 946. A third straight portion 940 of the sheath 930 extends from a distal end of the first curved portion 938, as shown in FIG. 18B. The sheath portions 934, 936, and 938 are arranged such that the angle between the plane of the first 934 and second 936 straight portions and the plane of the curved portion 938 are substantially orthogonal to each other. Variations on the orientation of the (1) first plane and the second plane, (2) the angle between the sheath straight portions, and/or (3) the angle between the curved sheath portion and the adjacent sheath straight portions, other than is shown here with respect to the sheathes in FIGS. 17A-17B, and 18A-18B, are contemplated as desired to optimize the movement that is used during a particular procedure. According to some embodiments, the sheath 930 may also include a removable tip, such as tip 912, at the distal end 930b.

According to one embodiment, a handle may be associated with any of the sheathes of FIGS. 14-16, 17A-17B, and 18A-18B during insertion, and the handle may extend over a portion of or the entirety of the first straight portion. For the sheathes shown in FIGS. 16, 17A-17B, and 18A-18B, preferably the distal straight portion and the curved portions are the only parts of the sheath that penetrate into a patient's body.

According to one embodiment, a hub containing medication may be inserted into the proximal end of any of the sheathes of FIGS. 14-16, 17A-17B, and 18A-18B.

The sheathes 860, 870, 880, 900, and 930 may be formed from a metal or a polymeric material. Examples of suitable metals include, but are not limited to, stainless steel, titanium, and alloys such as nitinol. Suitable polymers, which can be used as a coating on a metal to form the sheath, include but are not limited to, plastics such as polytetrafluoroethylene (PTFE). In some configurations, the sheath is rigid. However, in other configurations, the sheath is flexible.

In one illustrative embodiment, the surface of the sheath is smooth and may be coated with one or more drugs such as anesthetic, anti-inflammatory, coagulating, anticoagulating, antibiotic, or antimicrobial agents. The drug may be delivered to the patient's tissue while the sheath is in contact with the tissue. The surface of the sheath may be coated with a light-absorbing coating to reduce glare, for example, under a cystoscope. The coating may be a polymer, such as Teflon, or other suitable material, and may be colored to aid in detection. The surface of the sheath may be painted so that one can easily tell it apart from surrounding tissue and fluid under a cystoscope to make it easier to detect under the cystoscope.

The sheath may be at least partly hollow, and it may include a lumen (not shown) that has one or more openings on the sheath, for example, at the distal tip or along the side of the shaft. The cross-section of the sheath may have a constant shape and size, or its shape and/or size may vary along its length. The cross-section of the sheath may assume any suitable shape, for example, circular, semi-circular, oval, triangular, or rectangular. In other embodiments, the distal end may include an enlarged, flared portion to dilate tissue beyond the nominal diameter of the sheath.

Other exemplary sheathes are disclosed in U.S. Pat. No. 6,638,210, entitled "Surgical Apparatus and Methods for Delivery of a Sling in the Treatment of Female Urinary Incontinence," the contents of which are incorporated by reference herein in their entirety.

FIGS. 19A-19B, 20A-20B, and 21 are side-views of various delivery devices for use in delivering an implant to patient tissue. FIG. 19A shows a delivery device 950 having a straight shaft 952 and a handle 954. According to one embodiment, the handle 954 is optional, and the shaft 952 may be used without the handle 954. The handle has a proximal end 954a and a distal end 954b, and the shaft 952 has a proximal end 952a and a distal end 952b. The proximal end 952a of the shaft 952 extends from the distal end 954b of the handle 954. The distal end 952b of the shaft 952 includes an L-slot 960, as shown enlarged in FIG. 19B.

FIG. 19B is a side view of an L-slot 960 on a distal end 952b of a shaft 952 of a delivery device 950. The L-slot 960 is preferably formed from a first channel 960a approximately 2 mm in length and 1 mm in width extending radially into the shaft 952 and a second channel 960b approximately 5 mm in length and 1 mm in width extending distally along the length of the distal end 952b of the shaft 952 from an inner terminal end of the first channel 960a. In certain illustrative embodiments, an end termination member slides radially into the first channel 960a and along the second channel 960b to hook one end of an implant onto the distal end 952b of the shaft 952 of a delivery device 950.

An advantage of the L-slot 960 configuration is that the delivery device 950 may be used to pull an implant into place. During withdrawal of the delivery device 950, the distally extending orientation of the second channel 960b causes an associated end termination, such as end termination member 104, to slide to the distal most position in the L-slot 960. This tends to maintain the association between the end termination, and thus the implant, and the shaft 952, keeping the end termination member hooked into the second channel 960b during withdrawal of the delivery device. Additionally, the end termination member remains free to slide along the second channels 960b. When slid to a proximal-most position in the second channel 960b, the end termination member may be slid radially out of the first channel 960a to unhook the implant from the delivery device(s) with minimal effort.

According to one embodiment, the shaft 952 is inserted into a sheath, such as the sheath 860 of FIG. 14, and an end termination member of an implant is attached to the L-slot 960, allowing a user to drag the end termination member and the associated arm of an implant into the sheath by pulling the shaft 952 back out of the sheath. According to this embodiment, if the sheath is positioned in patient tissue and the end termination member of an implant is pulled through the sheath, dissociation of the implant from the delivery device and removal of the sheath will result in positioning of the arm of the implant in the location previously occupied by the sheath.

This process may be repeated with another end termination member on another arm of the implant, such as implant 780 shown in FIG. 10, using the same or a second delivery device.

In some alternative configurations, the second channel 960b of an L-slot 960 extends proximally, rather than distally, along the distal end of a shaft of any delivery device of the invention, and the shaft is used to push implant through the sheath. When pushing or inserting the shaft of the delivery device into the sheath, the proximally extending orientation of the second channel causes the end termination, for example the end termination member 104 as depicted in FIG. 1, to slide to a proximal most position in the L-slot. This tends to maintain the end termination, and thus the sling assembly comprising the end termination, hooked onto the second channel during insertion of the shaft of the delivery device into the sheath.

An alternative delivery device 970 for pushing an implant through a sheath, is shown in FIG. 20A. The delivery device 970 having a shaft 972 and a handle 974. According to one embodiment, the handle 974 is optional, and the shaft 972 may be used without the handle 974. The handle has a proximal end 974a and a distal end 974b, and the shaft 972 has a proximal end 972a and a distal end 972b. The shaft 972 includes a straight portion 978, extending from the distal end 974b of the handle 974, and a curved portion 980 extending from the distal end of the straight portion 978 to the distal end of the shaft 972b. The distal end 972b of the shaft 972 includes a reduced-diameter tip portion 984, as shown enlarged in FIG. 20B.

FIG. 20B shows an enlarged side view of the distal end 972b of the shaft 972 of FIG. 20A. The distal end 972b of the shaft 972, as shown in FIG. 20B, includes part of the curved portion 980, shoulder 988, and a reduced diameter tip-portion 984. According to one embodiment, the shaft 972 may couple with an end termination, such as end termination member 104 of FIG. 1 or end termination member 604 of FIG. 6, such that the ring of the end termination member slides down the tip-portion 984 until the ring abuts the shoulder 988. According to one embodiment, the shoulder 988 prevents passage of the ring of an end termination member past the reduced-diameter tip 984.

According to one embodiment, the tip-portion 984 has a constant cross-section. In another embodiment, the cross-section of the tip-portion tapers toward the distal end. In this embodiment, the tip-portion may be formed to interfit with an end termination member including a ring with a tapered inner surface.

Figure 21:
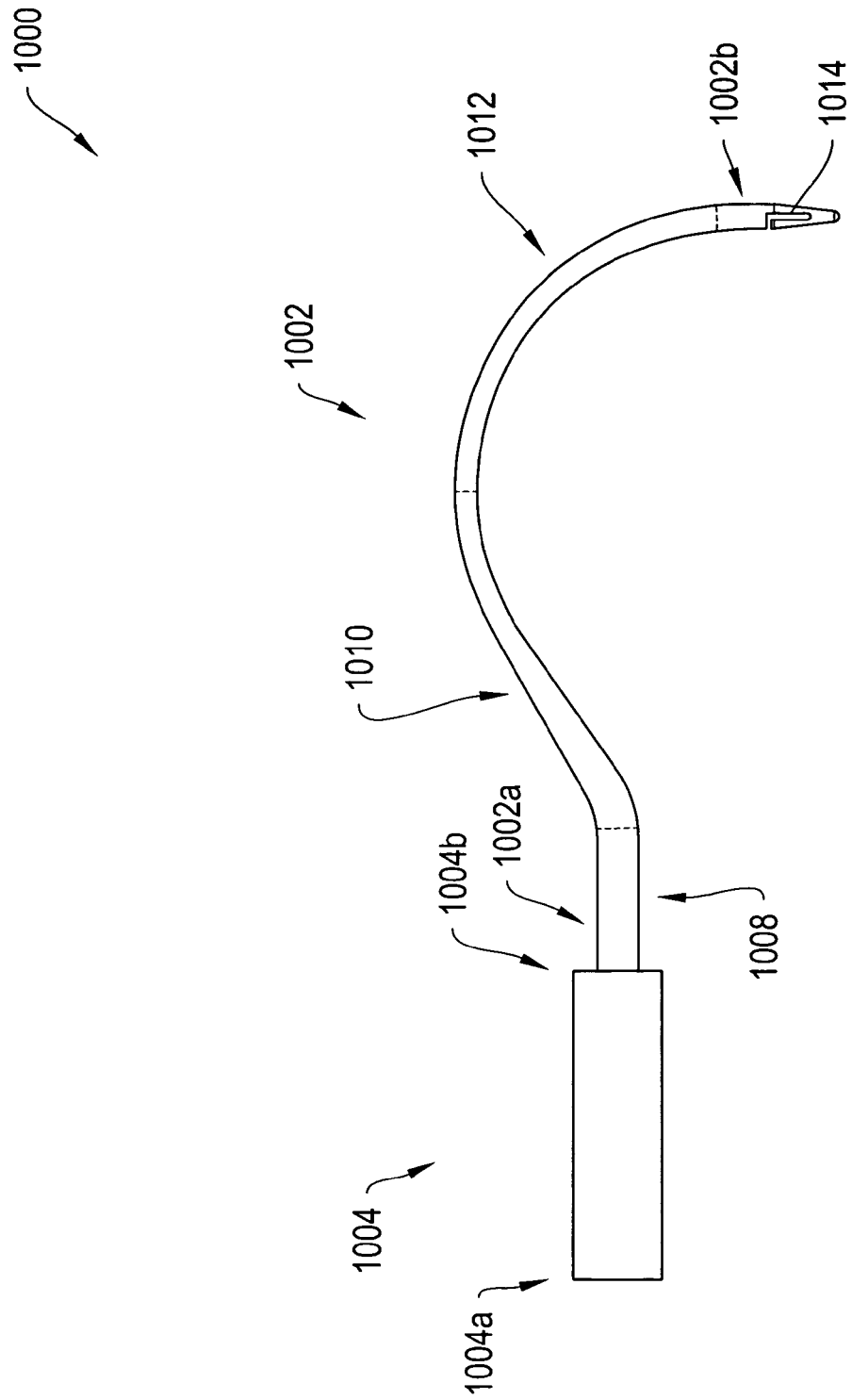
FIG. 21 is a side-view of a delivery device comprising a handle and a curved shaft, with an L-slot at the distal end of the shaft.

FIG. 21 depicts a side view of a delivery device 1000 including a shaft 1002 and a handle 1004. According to one embodiment, the handle 1004 is optional, and the shaft 1002 may be used in operation without the handle 1004. The handle 1004 has a proximal end 1004a and a distal end 1004b. The shaft 1002 extends from the distal end 1004b of the handle 1004, and has a proximal end 1002a and a distal end 1002b. The shaft 1002 includes a straight portion 1008 extending from the distal end of the handle 1004b, an upward-curving portion 1010, extending from the distal end of the straight portion 1008, and a downward-curving portion 1012, extending from the distal end of the upward-curving portion 1010 to the distal end 1002*b* of the shaft 1002. The distal end 1002*b* of the shaft includes an L-slot 1014, similar to the L-slot 960 shown enlarged in FIG. 19B.

According to various embodiments, the distal ends 952*b*, 972*b*, and 1002*b* of the shafts 952, 972, and 1002 of FIGS. 19A, 20A, and 21 may include any type of tip, including the L-slot 960 and the reduced-diameter tip 984 of FIGS. 19B and 20B, respectively. Furthermore, the shafts 952, 972, and 1002 may be attached to any type of handle, including for example, handles 954, 974, and 1004 of FIGS. 19A, 20A, and 21. In other embodiments, the shafts 952, 972, and 1002 may be used during an operative procedure without an associated handle. According to one embodiment, the shafts 952, 972, and 1002 shown in FIGS. 19A, 20A, and 21 all lie substantially in one plane.

According to one embodiment, in operation, the shafts 952, 972, and 1002 are inserted into associated sheathes, and used to pull or push an end termination member and associated implant arm through the sheath. In various embodiments, the sheathes and/or the shafts may be flexible, to allow a shaft, such as shafts 952, 972, and 1002 to pass through a sheath, such as sheathes 860, 870, 880, 900, and 930. Further delivery devices not shown herein, may include shafts shaped similarly to the sheathes 900 and 930 shown in FIGS. 17A and 18A, respectively.

Figure 22:
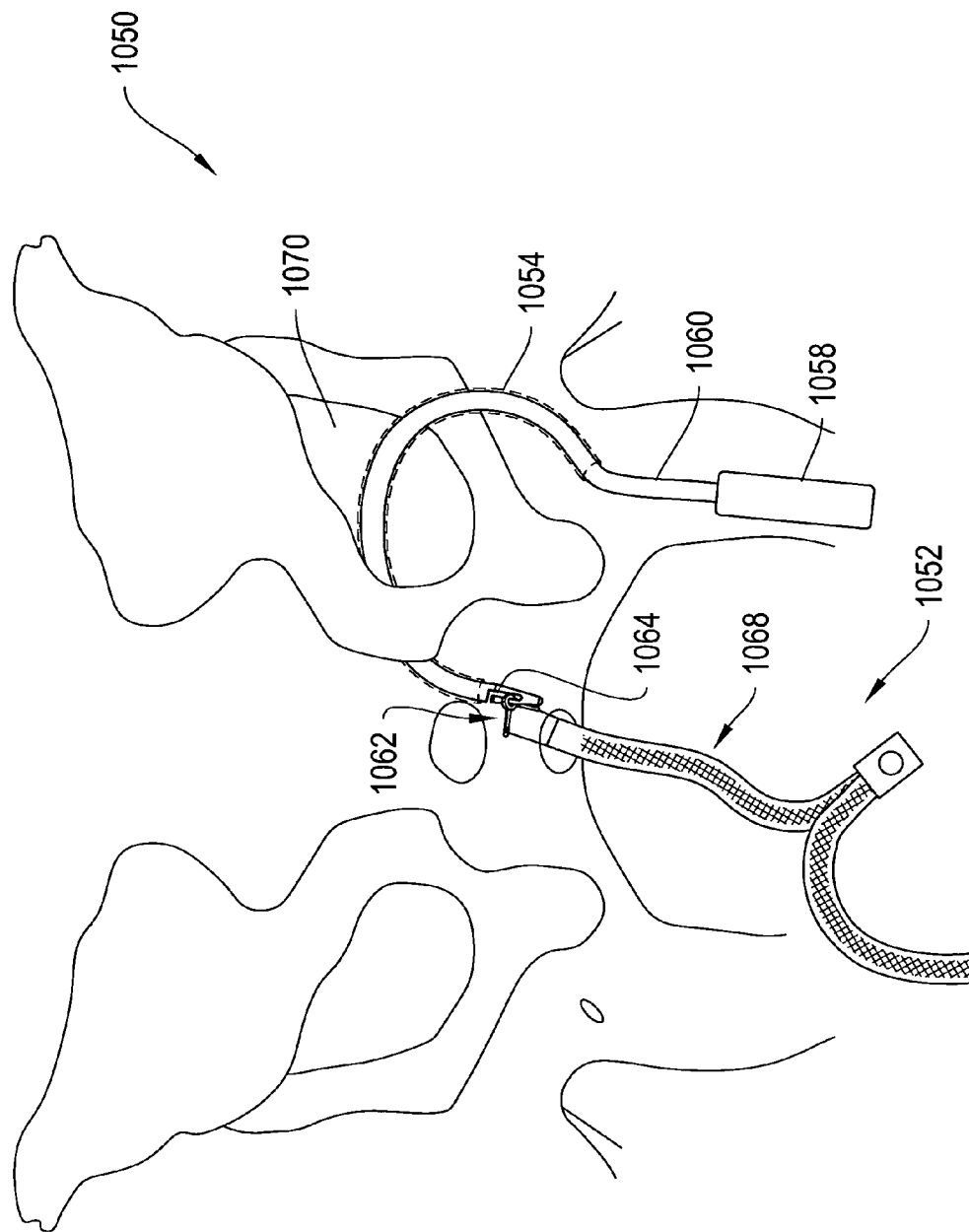
FIG. 22 shows an exemplary transobturator procedure for placement of an implant in patient tissue.
Figure 23:
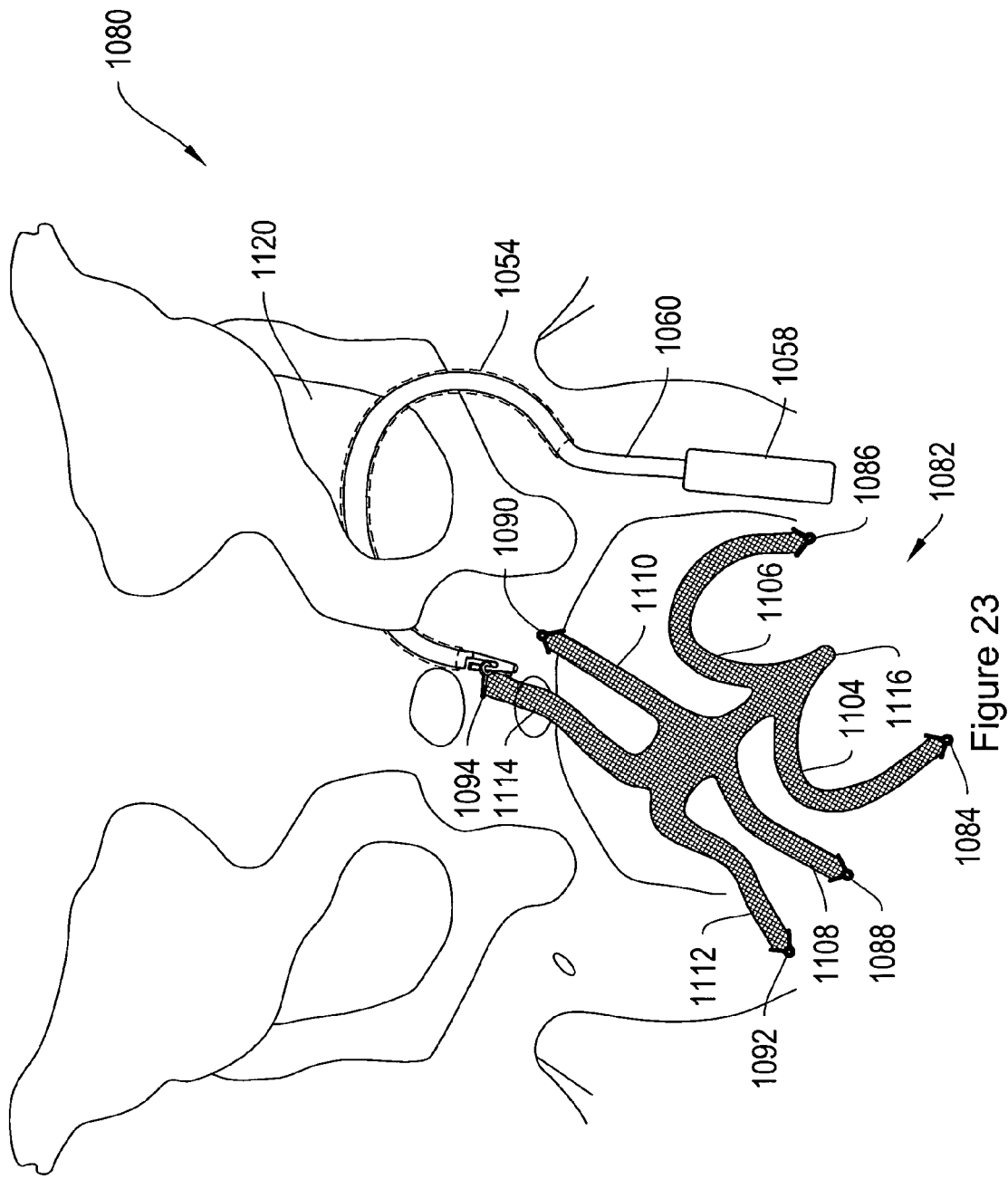
FIG. 23 shows another exemplary transobturator procedure for placement of an implant in patient tissue.

FIG. 22 shows aspects of an exemplary transobturator procedure 1050 for placement of an implant 1052 in patient tissue. The exemplary implant includes end termination members 1062 and 1066, similar to the end termination member 104 of FIG. 1. However, the end termination members 1062 and 1066 may be any suitable end termination members, such as end termination member 204 of FIG. 2, or end terminations 304, 404, 504, or 604 described above. FIG. 23 shows a similar procedure 1080 for placement of an implant 1082, similar to implant 780 of FIG. 10. The exemplary implant 1082 includes end termination members 1084, 1086, 1088, 1090, 1092, and 1094. In one embodiment, the implants 1052 and 1082 may include tanged mesh attachment straps, similar to the implant 840 of FIG. 12.

In the exemplary technique, the patient is placed on an operating table in a position to provide access to the pelvic region. The operator may subject the patient to local anesthesia, regional anesthesia, and/or general anesthesia or sedation according to his preference. Next, the operator makes a transverse incision (not shown) in the anterior vaginal wall of the patient and dissects the incision bilaterally according to his preference using, for example, surgical scissors. In certain implementations, the operator dissects bilaterally to the inferior pubic ramus on both sides of the patient. The incision may be made in the vagina so as to allow the inserted shaft to be near, contact, apply pressure to, or poke the skin at a position that is generally in line with the urethral meatus.

Next, the operator makes a vertical skin incision in the groin, large enough to insert the tip of the sheath just lateral to the edge of the inferior pubic ramus at the junction where the inferior pubic ramus and the adductor longus muscle meet. This may be repeated on the contralateral side. Thus, according to one implementation, for each side of the patient tissue, there are two incisions: a vaginal wall incision and a vertical skin incision.

Next, the operator accesses the patient's pelvic region via the two incisions to insert the implant into the patient's pelvic region and secure the implant within the region so that at least a portion of the implant is located posterior to the bladder-neck. According to the exemplary technique, to accomplish this, the operator inserts the sheath 1054 through a vertical skin incision, piercing through the obturator muscle and obturator membrane, toward the vaginal wall. The operator may hear and/or feel a pop indicating that he has pierced the obturator membrane. According one embodiment, for insertion, the distal end of the sheath 1054 may include a tip, such as tip 912 of FIG. 17B, and the proximal end of the sheath 1054 may be removably coupled to a handle, such as handles 954, 974, and 1004 of FIGS. 19, 20, and 21.

Once the sheath 1054 has passed through the obturator foramen 1070, the operator may turn the handle at a 45° angle medial toward the midline, and place the opposite hands forefinger into the lateral dissection of the vaginal incision, placing the fingertip on the distal end of the sheath 1054. In one implementation, the operator uses his fingertip to guide the distal end of the sheath around the inferior pubic ramus and through the vaginal incision, maintaining contact with the finger. The operator may palpate during delivery as preferred. The operator may also use the posterior portion of the patient's pubic bone as an anatomical landmark to assist in guiding the needle. According to one feature, after the sheath 1054 is in place, the optional tip and handle may be removed from the sheath 1054.

According to the exemplary technique, following sheath 1054 insertion, a shaft 1060 is inserted into the sheath 1054, such that the distal end of the shaft 1060, including the L-slot 1064, extends past the distal end of the sheath 1054. According to one embodiment, the shaft 1060 is flexible, easing insertion of the shaft 1060 into the sheath 1054.

According to an alternative embodiment, the shaft 1060 is inserted into the sheath 1054 before the sheath 1054 is inserted into patient tissue, and the shaft-sheath combination is inserted into the patient in a transobturator method as described above, such that the distal end of the sheath 1054 exits the tissue through the vaginal incision. In this embodiment, the sheath 1054 may be flexible and the shaft 1060 may be rigid.

In another embodiment, the sheath is inserted via an inside-out method. According to this method, the sheath is inserted first through the vaginal incision, then through the obturator foramen and toward the vertical skin incision. The shaft may then be inserted into the sheath via the outside-in method (toward the vaginal incision), as described above.

As shown in FIG. 22, the distal end of the shaft 1060 includes an L-slot 1064, similar to the L-slot 960 shown in FIG. 19B. After the operator inserts the sheath 1054 and the shaft 1060 into patient tissue, the L-slot 1064 extends beyond the distal end of the sheath 1054. The operator then hooks the end termination member 1062 of the implant 1052 on to the L-slot 1064, to couple the implant 1052 to the shaft 1060. The operator removes the shaft 1060 from the sheath 1054, for example by pulling handle 1058, thereby advancing the arm 1068 of the implant 1052 through the sheath 1054. According to one embodiment, the arms of the end termination member 1062 may be squeezed together to allow the end termination member 1062 to fit into and advance through the sheath 1054. Once the arm 1068 of the implant 1052 has been pulled through the sheath 1054, the end termination member 1062 of the implant 1052 is uncoupled from the shaft 1060, by sliding the ring of the end termination member 1062 out of the L-slot 1064. In one example, the arm 1068 includes anchoring tangs or projections as shown in the implants 840 and 850 of FIGS. 12 and 13, and the end termination member 1062 is removed (e.g., cut off) from the arm 1068. The sheath 1054 may then be removed from the patient, by pulling the proximal end of the sheath, leaving the arm 1068 of the implant 1052 in place. In one embodiment, this allows for implantation of a tanged mesh implant, such as implant 840 of FIG. 12, or an implant with lateral projections, such as implant 850 of FIG. 13, without unnecessary irritation of patient tissue such as may be caused by advancing a rough edge across patient tissue. The tangs or projections may act as a soft tissue anchor to anchor the arm in patient tissue. The operator repeats this process for the other end termination member 1066, inserting it on the contralateral side of the patient.

FIG. 23 shows aspects of an exemplary transobturator procedure 1080 for placement of an implant 1082 in patient tissue. The exemplary implant 1082 is substantially the same as the implant 780 shown in FIG. 10. The implant 1082 includes arms 1104, 1106, 1108, 1110, 1112, and 1114, and a posterior extension portion 1116. Attached to the distal end of each arm 1104, 1106, 1108, 1110, 1112, and 1114 of the implant 1082, is an end termination member 1084, 1086, 1088, 1090, 1092, and 1094, respectively. The end termination members 1084, 1086, 1088, 1090, 1092, and 1094 may be the same as the end termination member 204 of FIG. 2, or they may be any of the end terminations 104, 304, 404, 505, or 604 described above. According to one embodiment, an end termination member is also attached to the distal end of the posterior extension portion 1116. In one embodiment, the arms 1104, 1106, 1108, 1110, 1112, and 1114 are tanged, similar to the end portions 840a and 840b of the implant 840 of FIG. 12.

The implant arms 1104, 1106, 1108, 1110, 1112, and 1114 may each be delivered to a different location in the patient tissue using a variety of delivery approaches. According to one implementation, the anterior implant arms 1108, 1110, 1112, and 1114 are implanted using a transobturator procedure, as described above with respect to FIG. 22. FIG. 23 shows the placement of the arm 1114.

According to one embodiment, the location of the puncture of the obturator membrane within the obturator foramen 1120 depends on the implant arm 1104, 1106, 1108, 1110, 1112, or 1114 being delivered. For example, the operator delivers an anterior implant arm (e.g., implant arm 1114) through a sufficiently anterior region of the obturator foramen 1120 so that the implant 1082 extends to and supports anterior regions of the patient's pelvic floor, while the operator delivers a second anterior implant arm (e.g., the implant arm 1110) through a sufficiently posterior region of the obturator foramen 1120 so that the implant extends to the posterior regions of the patient's pelvic floor and provides posterior support. The implant arms 1108, 1110, 1112 and 1114 may be tanged or include projections, such as the implants 840 and 850 of FIGS. 12 and 13, and may be delivered using substantially the same method as described above with respect to the implant arm 1068 of FIG. 22. Thus, following insertion of each of the anterior arms 1108, 1110, 1112, and 1114 through the obturator foramen, the associated end termination members 1094, 1092, 1090, and 1088 are removed, and the tangs or projections act as soft tissue anchors, anchoring the arms 1108, 1110, 1112, and 1114 in patient tissue.

The posterior implant arm 1106 may be inserted using a different type of procedure that is not transobtural. In one implementation, the implant arm 1106 is inserted via a transgluteal procedure and secured through the sacrospinous ligament. To place the implant arm 1106, the operator makes an incision in the posterior vaginal wall and an appropriate lateral dissection to expose the sacrospinous ligament. The operator then makes a gluteal incision in the skin of the buttocks lateral to and below the anus, large enough to insert the tip of the sheath. A sheath is inserted into the gluteal incision, and through the sacrospinous ligament. In one embodiment, the sheath may extend through the sacrospinous ligament approximately 2 cm from the ischial spine. This is repeated on the contralateral side. Thus, according to one implementation, for each side of the patient tissue, there is a gluteal incision, and an exposure of the sacrospinous ligament by lateral dissection from the vaginal incision.

According to this implementation, the operator accesses the patient's pelvic region via the two incisions to insert the implant into the patient's posterior pelvic region. To accomplish this, the operator inserts the sheath through a gluteal incision, and through the sacrospinous ligament, toward the vaginal wall. According one embodiment, for insertion, the distal end of the sheath may include a tip, such as tip 912 of FIG. 17B, and the proximal end of the sheath may be removably coupled to a handle, such as handles 954, 974, and 1004 of FIGS. 19, 20, and 21. According to one feature, after the sheath is in place, the optional tip and handle are removed from the sheath.

According to the exemplary technique, following sheath insertion, a shaft is inserted into the sheath, such that the distal end of the shaft, including the L-slot, extends past the distal end of the sheath. According to one embodiment, the shaft is flexible to ease insertion of the shaft into the sheath.

According to an alternative embodiment, the shaft is inserted into the sheath before the sheath is inserted into patient tissue, and the shaft-sheath combination is inserted into the patient in a transgluteal method as described above, such that the distal end of the sheath exits the tissue through the vaginal incision. In this embodiment, the sheath may be flexible and the shaft may be rigid.

In another embodiment, the sheath is inserted via an inside-out method. According to this method, the sheath is inserted through the vaginal incision and then through the sacrospinous ligament, toward the gluteal incision.

In certain implementations, the distal end of the shaft includes an L-slot, similar to the L-slot 960 shown in FIG. 19B. After the operator inserts the sheath and the shaft into patient tissue, the L-slot extends beyond the distal end of the sheath. The operator then hooks the end termination member 1086 of the implant 1082 on to the L-slot, to couple the implant 1082 to the shaft. The operator removes the shaft from the sheath, for example by pulling handle, thereby advancing the arm 1106 of the implant 1082 through the sheath. Once the arm 1106 of the implant 1082 has been pulled through the sheath, the end termination member 1086 of the implant 1082 is uncoupled from the shaft, by sliding the ring of the end termination member 1086 out of the L-slot. In one example, the arm 1106 includes anchoring tangs or projections as shown in the implants 840 and 850 of FIGS. 12 and 13, and the end termination member 1086 is removed (e.g., cut off) from the arm 1106. The sheath may then be removed from the patient, by pulling the proximal end of the sheath, leaving the arm 1106 of the implant 1082 in place. This may allow for implantation of a tanged mesh implant, or an implant with tanged mesh arms, such as the arms of the implant 840 of FIG. 12, or an implant with arms having lateral projections, such as implant 850 of FIG. 13, without unnecessary irritation of patient tissue such as may be caused by advancing a rough edge across patient tissue. The tangs or projections may act as a soft tissue anchor, to anchor the arm in patient tissue.

Figure 24:
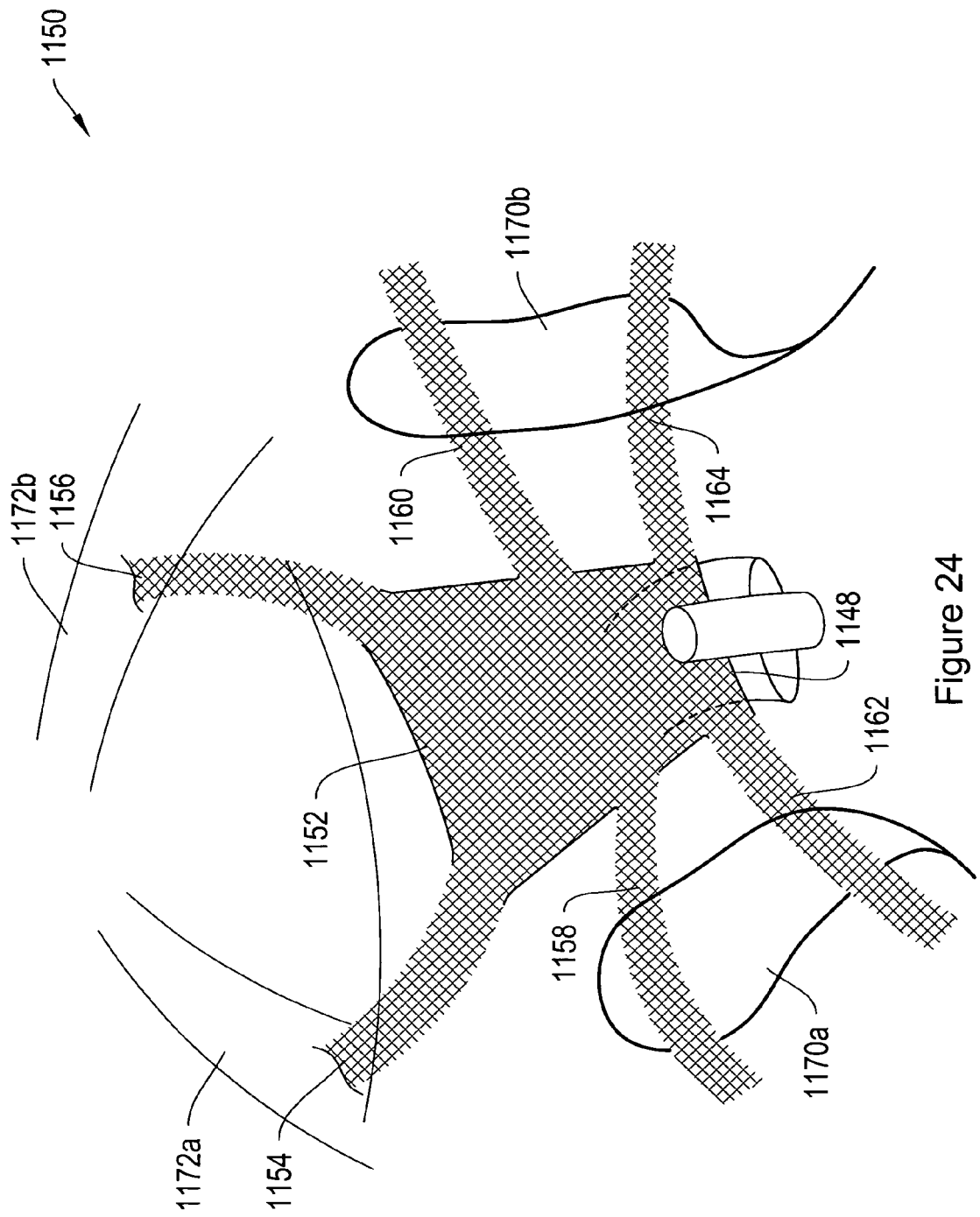
FIG. 24 shows an exemplary pelvic floor implant positioned in patient tissue.

FIG. 24 shows an exemplary implant 1150 positioned in the pelvic floor tissue of a patient. The implant 1150 includes a center portion 1152, posterior arms 1154 and 1156, and anterior arms 1158, 1160, 1162, and 1164. The anterior arms 1158 and 1162 are inserted into the right obturator foramen 1170a, while the anterior arms 1160 and 1164 are inserted into the left obturator formation 1170b. The posterior arms 1154 and 1156 are inserted into the right 1172a and left 1172b sacrospinous ligaments, respectively. In the illustrative example, the arms 1154, 1156, 1158, 1160, 1162, and 1164 include tangs that anchor the implant 1150 in the patient's tissue.

In certain implementations, the operator generally delivers the implant 1082 along a path that avoids certain pelvic structures, such as the internal pudendal artery, the pudendal canal, the perineal nerve, the labial nerve, and other vascular and nerve structures.

In one embodiment, any of the arms of the implant may be delivered using a single incision procedure. For example, the anterior arms may be delivered via a transvaginal procedure, in which the arms are extended toward target locations in the obturator foramen and anchored in place with a soft tissue anchor. The posterior arms may be delivered transvaginally to target locations in the sacrospinous ligament and anchored in place with a soft tissue anchor.

According to an alternative embodiment, the end termination 1090 and the associated arm 1110 is inserted into a target region of the levator ani muscle, such as into the tendinous arch of the levator ani muscle. This procedure is described in greater detail with respect to the above-mentioned reference "Systems, Devices and Methods for Treating Pelvic Floor Disorder" (U.S. application Ser. No. 11/400,111).

According to various embodiments, different sheaths and/or shafts may be used to insert different arms of an implant. For example, the six arms of implant 1082 of FIG. 23 may each be inserted using a different method and/or a different sheath and/or delivery device. According to one embodiment, a separate delivery device and a separate sheath are used for each arm of an implant.

Exemplary mesh materials that may be used for the slings and, as applicable, any of the support legs include, for example, synthetic materials, natural materials (e.g., biological) or a combination thereof. The mesh may be fabricated from any of a number of biocompatible materials, such as nylon, silicone, polyethylene, polyester, polyethylene, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), poly(amino acids), polypeptides, human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, having a single direction where the tensile strength of the material is the highest. Oriented materials may include rectus fascia and/or facia lata. In addition to those listed above, exemplary biodegradable polymers which may be used to form the slings or, as applicable, the arms disclosed herein, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly (L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as poly(lysine), Poly(glutamic acid), gelatin and collagen; and mixtures and copolymers thereof.

The sling assemblies, including the various slings and, as applicable, the arms disclosed herein, may include an agent for release into the patient's tissues. One illustrative agent is a tissue growth factor that, when applied to the patient's tissues in a pharmaceutically acceptable amount, promotes well-organized collagenous tissue growth, such as scar tissue growth, preferably, in large quantities. According to one feature, the agent may or may not block or delay the dissolvability of the biodegradable materials. Whether or not an agent blocks or delays such dissolvability may be controlled by selecting differing methods for loading the agent onto the sling. Exemplary tissue growth factors may include natural and/or recombinant proteins for stimulating a tissue response to enhance collagenous tissue growth. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenylbutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

According to another feature, the slings disclosed herein may include any suitable end portions, such as tissue dilators, anchors, and association mechanisms for associating the sling with a delivery device. Without limitation, examples of slings, sling assemblies, sling delivery devices and approaches, sling assembly-to-delivery device association mechanisms, and sling anchoring mechanisms including features with which the slings and sling assemblies of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof." Moreover, the slings disclosed herein may be adapted for use in pelvic floor repair systems and related devices and methods. Such systems include, for example, those disclosed in U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,212, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," and U.S. patent application Ser. No. 11/115,655, entitled "Surgical Implants and Related Methods," U.S. patent application Ser. No. 11/400,111, entitled "Systems, Devices, and Methods for Treating Pelvic Floor Disorders," and U.S. patent application Ser. No. 11/399,913, entitled "Systems, Devices, and Methods for Sub-Urethral Support," the entire contents of all of which are incorporated herein by reference.

The foregoing embodiments are merely examples of various configurations of the materials described and disclosed herein. Additional configurations can be readily deduced from the foregoing, including combinations thereof, and such configurations and continuations are included within the scope of the invention. The specifications and other disclosures in the patents, patent applications, and other references cited herein are hereby incorporated by reference in their entirety.

What is claimed is:

1. A method for delivering an implant to a patient, comprising:
    inserting a sheath having a hollow center into an incision in the patient; inserting a shaft of a delivery device into the center of the sheath;
    associating an end termination member of the implant with a slot in the shaft; advancing the shaft and the associated implant through the sheath; and
    anchoring the implant in the soft tissue of the patient's pelvic floor region through one or more tangs of the implant.

2. The method of claim 1, comprising pulling the end termination member through the sheath.

3. The method of claim 1, comprising pushing the end termination member through the sheath.

4. The method of claim 1, comprising inserting the shaft into the sheath prior to inserting the sheath into the incision.

5. The method of claim 1, comprising removing the sheath from the patient.

6. The method of claim 5, comprising anchoring the end termination member in the soft tissue of the patient's pelvic floor region.

7. The method of claim 1, comprising removing the end termination member from the implant.

8. The method of claim 1, comprising inserting the sheath through the patient's gluteus maximums.

9. The method of claim 1, comprising inserting the sheath through the sacrospinous.

* * * * *